United States Patent
Lindenschmidt et al.

(10) Patent No.: US 7,488,818 B2
(45) Date of Patent: Feb. 10, 2009

(54) METHOD FOR PRODUCING 1,4-DIPHENYL AZETIDINONE DERIVATIVES

(75) Inventors: Andreas Lindenschmidt, Bad Soden (DE); David William Will, Kriftel (DE); Gerhard Jaehne, Frankfurt (DE); Theodor Andreas Wollmann, Hattersheim (DE); Wendelin Frick, Hunstetten-Beuerbach (DE); Bernd Junker, Bad Soden (DE); David Rigal, Kriftel (DE); Guenter Billen, Niedernhausen (DE); Heiner Jendralla, Heiner (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 11/561,626

(22) Filed: Nov. 20, 2006

(65) Prior Publication Data

US 2007/0149776 A1    Jun. 28, 2007

Related U.S. Application Data

(63) Continuation of application No. PCT/EP2005/005498, filed on May 20, 2005.

(30) Foreign Application Priority Data

May 21, 2004    (DE)    ........................ 10 2004 025 071
Mar. 9, 2005    (DE)    ........................ 10 2005 010 770

(51) Int. Cl.
*C07D 205/08* (2006.01)
*C07F 9/6503* (2006.01)
*C07F 9/6506* (2006.01)
*C07F 9/6541* (2006.01)
*C07F 9/653* (2006.01)
*C07F 9/572* (2006.01)
*C07F 9/54* (2006.01)

(52) U.S. Cl. ........................ 540/200; 548/208; 548/229; 548/243; 548/335.1; 548/366.4; 548/473; 548/545; 568/11

(58) Field of Classification Search ................. 540/200
See application file for complete search history.

(56) References Cited

U.S. PATENT DOCUMENTS 5,306,817 A * 4/1994 Thiruvengadam et al. ... 540/200
5,631,365 A    5/1997 Rosenblum et al.

FOREIGN PATENT DOCUMENTS

| EP | 1362855 | 11/2003 |
|----|---------|---------|
| WO | WO 93/02048 | 2/1993 |
| WO | WO 95/01961 | 1/1995 |
| WO | WO 95/08532 | 3/1995 |
| WO | WO 02/50027 | 6/2002 |

* cited by examiner

*Primary Examiner*—Mark L Berch
(74) *Attorney, Agent, or Firm*—Craig M. Bell

(57) ABSTRACT

The present invention is directed to the preparation of novel compounds useful in the treatment of hyperlipidemia, arteriosclerosis, hypercholesterolemia, and other related metabolic disorders. More specifically, the present invention is a novel process for the preparation of 1,4-diphenylazetidinone derivatives from β-substituted amino amides which are protected in the presence of silylating agents and at least one cyclization catalyst whose structural formula is represented by one of the general formula:

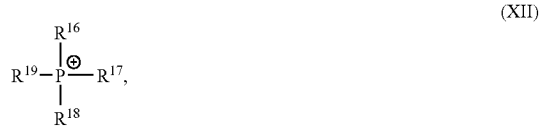

(XII)

wherein the various R-groups are defined herein.

15 Claims, No Drawings

METHOD FOR PRODUCING 1,4-DIPHENYL AZETIDINONE DERIVATIVES

The invention relates to the preparation of 1,4-diphenylazetidinone derivatives by cyclization of β-substituted amino amides in the presence of silylating agents and cyclization catalysts.

Ezetimibe as known representative of these compounds blocks the absorption of cholesterol from the intestine, so that both lower LDL levels and fewer triglycerides are observed in patients. Specifically, it is 1-(4-fluorophenyl)-3(R)-[3-(4-fluorophenyl)-3(S)-hydroxypropyl]-4(S)-(4-hydroxyphenyl)-2-azetidinone of the following formula (see claim 8 in EP 0 720 599 B1).

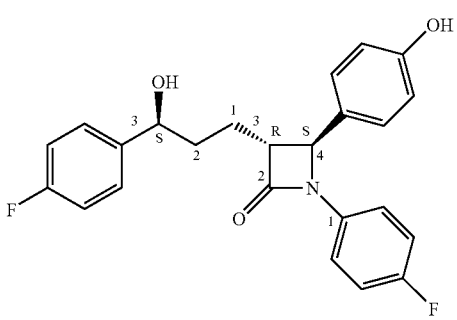

Concerning this compound itself, some chemical modifications, their preparation by various process variants and their therapeutic use for the treatment of hyperlipidemia and of arteriosclerosis and hypercholesterolemia, inter alia the following publications have appeared, attempts having been made for example to find chemical modifications of comparable therapeutic effect but with less intestinal absorption.

EP 0 524 595 A1 describes chemical modifications of ezetimibe of the general formula

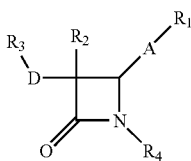

which may inter alia also have a second substituent ($R_2$) in position 3 of the azetidinone ring, also have connecting moieties (A) between the phenyl ring in position 4 of the azetidinone ring and the ring, and have no or other substituents instead of the fluorine groups on the phenyl rings ($R_3$, $R_4$). The compounds are synthesized (e.g. for $R_2$=H) by cyclization of hydroxy amides of the general formulae

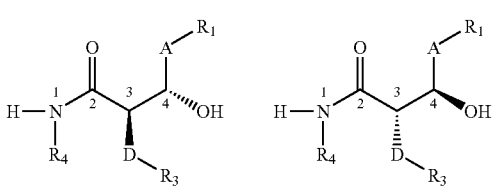

with, for example, trialkylphosphine/dialkyl azodicarboxylate, dialkyl chlorophosphate/phase-transfer catalyst, di- or trichlorobenzoyl chloride/tetra-n-butylammonium hydrogen sulfate, or dichlorobenzoyl chloride/NaH.

However, these synthetic routes are unsuitable for an industrial process because, for example, dialkyl azodicarboxylates are explosive and dialkyl chlorophosphates are extremely toxic. In the syntheses using di- or trichlorobenzoyl chlorides it is necessary to employ either tetra-n-butylammonium hydrogen sulfate in stoichiometric amounts or NaH which is difficult to handle in large quantities, neither of which is suitable for an industrial process.

A further synthesis described in EP 0 524 595 A1 proceeds by reacting carboxylic acids of the general formula

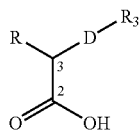

or by a comparable reaction but with a carboxylic acid derivative, e.g. an acid chloride or mixed anhydride, with chiral oxazolidinones, to give compounds of the general formula

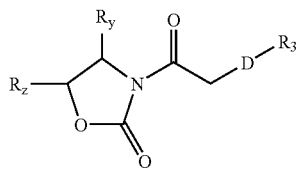

where $R_y$, $R_z$ are for example independently of one another H, $C_1$-$C_6$-alkyl, phenyl, benzyl.

In a modification of the preparation of the above hydroxy amides, compounds of the above general formula are condensed with imines in the presence of $TiCl_4$ and TMEDA (tetramethylethylenediamine)

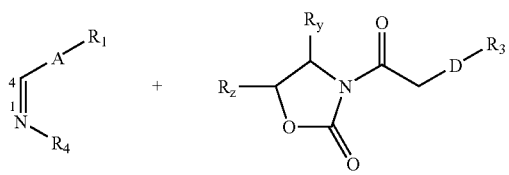

to give compounds of the general formula below.

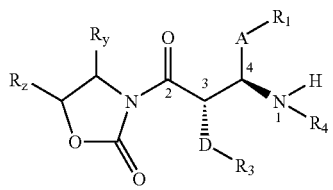

and cyclized of the further reaction with Na bistrimethylsilylamide and Li bistrimethylsilylamide to give

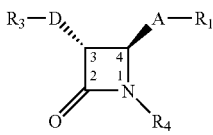

However, TMEDA may on repeated contact induce dermatitis and is highly water-endangering. In addition, the cyclization must be carried out with Na bistrimethylsilylamide or Li bistrimethylsilylamide at low temperatures (−78° C.) because, otherwise, considerable amounts of byproduct are formed. This synthetic route is therefore unsuitable for an industrial process.

EP 0 707 567 B1 discloses a specific process for preparing azetidinone derivatives in which (Q=H or, for example, alkyl)

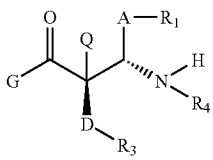

β-substituted amino amides of the above formula, which are protected in a suitable manner and in which G is inter alia one of the following radicals

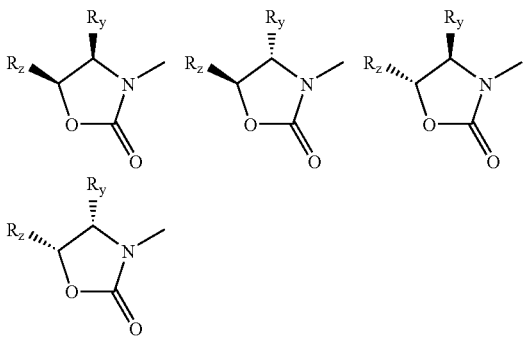

are reacted with a silylating agent and a fluoride ion catalyst as cyclizing agent or with a salt of the chiral compound (G⁺ salt), in particular with bis(trimethylsilyl)acetamide and tetra-n-butylammonium fluoride.

A particular disadvantage of this process route derives from the use of toxic and highly water-endangering TBAF. In addition, the hygroscopic nature of TBAF constitutes a problem because considerable amounts of a hydrolysis product are formed if the water content of the reaction solution is too high.

Further compound modifications of diphenylazetidinone derivatives are described for example in WO 02/50027, wherein at least one of the substituents on the 3 phenyl radicals present in the molecule is a $(C_1-C_{30})$-alkylene-(LAG) radical in which one or more C atoms of the alkylene radical may be replaced by, for example, —O—, —CH=CH— or —NR— (R=H, $C_1$-$C_6$-alkyl, $C_1$-$C_6$-alkylphenyl) and LAG is for example a saccharide, disaccharide, trisaccharide, amino acid or oligopeptide residue.

WO 02/066464 describes further modifications of compounds of the 1,4-diphenylazetidinone type which are prepared by cyclization of compounds of the general formula

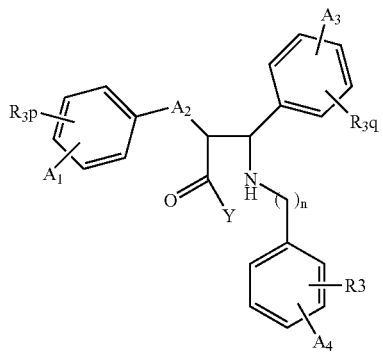

($A_1$, $A_3$ and $A_4$ are, for example, H, halogen, $C_1$-$C_5$-alkyl; $A_2$ is, for example, a $C_1$-$C_5$-alkylene chain or $C_1$-$C_5$-alkenylene chain; R3 is, for example, OH, OC(O)—$R_1$ with $R_1$ for example H or ($C_1$-$C_5$)alkyl; n, p, q, r are either zero or a multiple of 1 or 2; Y is an optically active sultam derivative) with TBAF and a silylating agent.

Owing to the toxicity and highly water-endangering nature of TBAF, this process is likewise not advantageous.

It is an object of the invention to indicate further synthesis variants for the aforementioned compounds, which can also be carried out stereospecifically and in high yield, and requires auxiliary reagents which have minimal toxicity. With a view to use in an industrial process, it should also be possible to carry it out with catalytic amounts of cyclization reagent.

One achievement is then a process for preparing 1,4-diphenylazetidinone derivatives from β-substituted amino amides which are protected in a suitable way in the presence of silylating agents and at least one cyclization catalyst, this cyclization catalyst being represented by one of the general formulae below (XII)

as cation, where $R^{16}$, $R^{17}$, $R^{18}$ and $R^{19}$ are independently of one another aryl, $(C_1-C_{15})$alkyl or benzyl, $R^{41}$ is aryl, $(C_1-C_{15})$alkyl or benzyl, $R^{42}$ is $(C_1-C_{15})$alkyl, benzyl, $(C_5-C_8)$cycloalkyl or aryl, where aryl may be substituted by F, Cl, Br, I, —OH, —O($C_1$-$C_3$)alkyl, —NH$_2$, —NH($C_1$-$C_3$)alkyl, —N[($C_1$-$C_3$)alkyl]$_2$, —C(O)OH, —C(O)O($C_1$-$C_3$)alkyl, —C(O)NH$_2$, —C(O)NH($C_1$-$C_3$)alkyl, —C(O)N[($C_1$-$C_3$)alkyl]$_2$, —SO$_2$NH$_2$, —SO$_2$NH($C_1$-$C_3$)alkyl, —SO$_2$N[($C_1$-$C_3$)alkyl]$_2$—CN, $(C_1$-$C_{12})$alkyl or $(C_5$-$C_8)$cycloalkyl, and (VIII)

or

-continued $$\begin{array}{c} Z_n\diagup\overset{R}{\underset{}{\diagdown}}\diagdown T \\ | \quad\quad\quad | \\ \ominus N\diagdown\underset{Q}{\diagup}M_n \end{array}$$ or (IX)

$$\begin{array}{c} Z_n\diagup\overset{R}{\underset{}{\diagdown}}\diagdown T \\ | \quad\quad\quad | \\ \ominus N\diagdown\underset{V}{\diagup}U \end{array}$$ or (X)

$$\ominus N\diagup\overset{R^{40}}{\underset{R^{39}}{\diagdown}S\diagdown\overset{O}{\underset{O}{\diagdown}}}$$ (XI)

as anion, and the symbols, substituents and indices have the following meaning, $Z=C=O$, $C=S$, $S=O$, $SO_2$ or $C=NR^{20}$
$K=O$, $S$, $NR^{21}$ or $CR^{22}R^{23}$
$L=NR^{24}$ or $CR^{25}R^{26}$
$n=0$ or $1$
$M=O$, $C=O$, $NR^{27}$ or $CR^{28}R^{29}$
$Q=O$, $S$, $NR^{30}$, $CR^{31}R^{32}$, $C=O$, $C=S$, $S=O$, $SO_2$ or $C=NR^{34}$
$R=CR^{35}$ or $N$
$T=CR^{36}$ or $N$
$U=CR^{37}$ or $N$
$V=CR^{38}$ or $N$ where $R^{20}$ to $R^{32}$ and $R^{34}$ to $R^{38}$ are independently of one another H, $(C_1\text{-}C_6)$alkyl, aryl or heteroaryl, and in each case two alkyl radicals may together also form a cycloalkylene radical with a maximum of 6 C units in the ring which may in turn be substituted by F, Cl, Br, I, $CF_3$, $NO_2$, $COO(C_1\text{-}C_6)$alkyl, $CON[(C_1\text{-}C_6)\text{alkyl}]_2$, cycloalkyl, $(C_1\text{-}C_{10})$alkyl, $(C_2\text{-}C_6)$alkenyl, $O-(C_1\text{-}C_6)$alkyl, $O-CO-(C_1\text{-}C_6)$alkyl, $O-CO-(C_1\text{-}C_6)$alkylene-aryl, $SO_2N[(C_1\text{-}C_6)\text{alkyl}]_2$, $S-(C_1\text{-}C_6)$alkyl, $S-(CH_2-)_n$aryl, $SO-(C_1\text{-}C_6)$alkyl, $SO-(CH_2-)_n$aryl, $SO_2-(C_1\text{-}C_6)$alkyl, $SO_2-(CH_2-)_n$aryl, $SO_2-N((C_1\text{-}C_6)\text{alkyl})(CH_2-)_n$aryl, or $SO_2-N((CH_2-)_n\text{aryl})_2$, where n may be 0 to 6, and the aryl radical may be substituted up to twice by F, Cl, Br, $CF_3$, $SF_5$, $NO_2$, $OCF_3$, $O-(C_1\text{-}C_6)$alkyl or $(C_1\text{-}C_6)$alkyl;

or by $N((C_1\text{-}C_6)\text{alkyl})_2$, $NH-CO-NH-(C_1\text{-}C_6)$alkyl), $NH-CO-NH$-aryl, $N[(C_1\text{-}C_6)\text{alkyl}]\text{-}CO-(C_1\text{-}C_6)$alkyl, $N[(C_1\text{-}C_6)\text{alkyl}]\text{-}COO-(C_1\text{-}C_6)$alkyl, $N[(C_1\text{-}C_6)\text{alkyl}]\text{-}CO$-aryl, $N[(C_1\text{-}C_6)\text{alkyl}]\text{-}COO$-aryl, $N[(C_1\text{-}C_6)\text{alkyl}]\text{-}CO-N((C_1\text{-}C_6)\text{alkyl})_2$, $N[(C_1\text{-}C_6)\text{alkyl}]\text{-}CO-N((C_1\text{-}C_6)\text{alkyl})$-aryl, $N[(C_1\text{-}C_6)\text{alkyl}]\text{-}CO-N(\text{aryl})_2$, $N(\text{aryl})\text{-}CO-(C_1\text{-}C_6)$ alkyl, $N(\text{aryl})\text{-}COO-(C_1\text{-}C_6)$alkyl, $N(\text{aryl})\text{-}CO$-aryl, $N(\text{aryl})\text{-}COO$-aryl, $N(\text{aryl})\text{-}CO-N((C_1\text{-}C_6)\text{alkyl})_2$, $N(\text{aryl})\text{-}CO-N[((C_1\text{-}C_6)\text{alkyl}]$-aryl, $N(\text{aryl})\text{-}CO-N(\text{aryl})_2$, aryl, $O-(CH_2-)_n$aryl, where n may be 0 to 6, where the aryl radical may be substituted 1 to 3 times by F, Cl, Br, I, $CF_3$, $NO_2$, $OCF_3$, $O-(C_1\text{-}C_6)$alkyl, $(C_1\text{-}C_6)$alkyl, $N((C_1\text{-}C_6)\text{alkyl})_2$, $SF_5$, $SO_2-CH_3$ or $COO-(C_1\text{-}C_6)$alkyl and where $R^{39}$ and $R^{40}$ are independently of one another $(C_1\text{-}C_6)$alkyl, where one or more nonadjacent C atoms may be replaced by NH or $C=O$, or are $(C_1\text{-}C_6)$perfluoroalkyl, aryl or heteroaryl, or $R^{39}$ and $R^{40}$ form together a 1,8-naphthyl or 1,7,7-trimethylbicyclo[2.2.1]heptanyl, $R^{40}$ may also be H, or where the cation in this cyclization catalyst corresponds to that of the general formula (XII), and the anion is $R^{41}O^-$ or where the cation in this cyclization catalyst corresponds to that of the general formula (XII), and the anion is $R^{42}COO^{-1}$, or where the cation in this cyclization catalyst corresponds to the general formula (XII), and the anion is $Cl^-$, $Br^-$ or $I^-$, and these are combined with $Ag_2O$.

Aryl means in this connection an aromatic hydrocarbon radical which has 6 to 14 C atoms, e.g. phenyl, naphthyl-, biphenyl-, tetrahydronaphthyl-, alpha- or beta-tetralon-, indanyl- or indan-1-on-yl radical and is preferably unsubstituted, but may also be substituted.

Typical substituents in this connection are, for example, F, Cl, Br, I, $CF_3$, $NO_2$, $COO(C_1\text{-}C_6)$alkyl, $CON[(C_1\text{-}C_6)\text{alkyl}]_2$, cycloalkyl, $(C_1\text{-}C_{10})$alkyl, $(C_2\text{-}C_6)$alkenyl, $O-(C_1\text{-}C_6)$alkyl, $O-CO-(C_1\text{-}C_6)$alkyl, $O-CO-(C_1\text{-}C_6)$alkylene-aryl, $SO_2N[(C_1\text{-}C_6)\text{alkyl}]_2$, $S-(C_1\text{-}C_6)$alkyl, $S-(CH_2-)_n$aryl, $SO-(C_1\text{-}C_6)$alkyl, $SO-(CH_2-)_n$aryl, $SO_2-(C_1\text{-}C_6)$alkyl, $SO_2-(CH_2-)_n$aryl, $SO_2-N((C_1\text{-}C_6)\text{alkyl})(CH_2-)_n$aryl, or $SO_2-N((CH_2-)_n\text{aryl})2$, where n may be 0 to 6, and the aryl radical may be substituted up to twice by F, Cl, Br, $CF_3$, $SF_5$, $NO_2$, $OCF_3$, $O-(C_1\text{-}C_6)$alkyl or $(C_1\text{-}C_6)$alkyl; or else $N((C_1\text{-}C_6)\text{alkyl})_2$, $NH-CO-NH-(C_1\text{-}C_6)$alkyl), $NH-CO-NH$-aryl, $N[(C_1\text{-}C_6)\text{alkyl}]\text{-}CO-(C_1\text{-}C_6)$alkyl, $N[(C_1\text{-}C_6)\text{alkyl}]\text{-}COO-(C_1\text{-}C_6)$alkyl, $N[(C_1\text{-}C_6)\text{alkyl}]\text{-}CO$-aryl, $N[(C_1\text{-}C_6)\text{alkyl}]\text{-}COO$-aryl, $N[(C_1\text{-}C_6)\text{alkyl}]\text{-}CO-N((C_1\text{-}C_6)\text{alkyl})_2$, $N[(C_1\text{-}C_6)\text{alkyl}]\text{-}CO-N((C_1\text{-}C_6)\text{alkyl})$-aryl, $N[(C_1\text{-}C_6)\text{alkyl}]\text{-}CO-N(\text{aryl})_2$, $N(\text{aryl})\text{-}CO-(C_1\text{-}C_6)$ alkyl, $N(\text{aryl})\text{-}COO-(C_1\text{-}C_6)$alkyl, $N(\text{aryl})\text{-}CO$-aryl, $N(\text{aryl})\text{-}COO$-aryl, $N(\text{aryl})\text{-}CO-N((C_1\text{-}C_6)\text{alkyl})_2$, $N(\text{aryl})\text{-}CO-N[((C_1\text{-}C_6)\text{alkyl}]$-aryl, $N(\text{aryl})\text{-}CO-N(\text{aryl})_2$, aryl, $O-(CH_2-)_n$aryl, where n may be 0 to 6, where the aryl radical may be substituted 1 to 3 times by F, Cl, Br, I, $CF_3$, $NO_2$, $OCF_3$, $O-(C_1\text{-}C_6)$alkyl, $(C_1\text{-}C_6)$alkyl, $N((C_1\text{-}C_6)\text{alkyl})_2$, $SF_5$, $SO_2-CH_3$ or $COO-(C_1\text{-}C_6)$alkyl Heteroaryl means in this connection aromatic rings and ring systems which, apart from carbon, also comprise heteroatoms such as nitrogen, oxygen or sulfur. Ring systems in which the heterocyclic radical is fused to benzene nuclei also belong to this definition. The rings preferably have 3 to 7 members.

An alkyl radical means a straight-chain or branched hydrocarbon chain having one or more carbons, preferably 1 to 8 carbons, e.g. methyl, ethyl, propyl, butyl, hexyl, isopropyl, isobutyl, neopentyl, tert-butyl, hexyl.

A cycloalkyl radical means a radical consisting of a ring system which comprises one or more rings and which is saturated or partially unsaturated (with one or two double bonds) and which is exclusively composed of carbon atoms, e.g. cyclopropyl, cyclopentyl, cyclopentenyl, cyclohexyl or adamantyl. The rings preferably have 3 to 7 members. The aforementioned substituents are typical possibilities.

A preferred embodiment of the process of the invention starts from the known process for preparing 1,4-diphenylazetidinone derivatives of the general formula (I)

(I)

in which the symbols, substituents and indices have the following meaning, $X=CH_2$, CHOH, CO or $CHOCOR^{11}$ $R^1$, $R^2$=independently of one another H, OH, $OCF_3$, or O—$(C_1-C_6)$alkyl, O—$(C_3-C_7)$cycloalkyl, O—$COR^{11}$, CN, $CH_2NHR^7$, $CH_2NR^7R^8$, $NR^7R^8$, $COR^{14}$, F or Cl $R^3$, $R^4$=independently of one another H, F, Cl, OH, $OCF_3$, O—$(C_1-C_6)$alkyl, O—$(C_3-C_7)$cycloalkyl, O—$COR^{11}$, CN, $CH_2NHR^7$, $CH_2NR^7R^8$, $NR^7R^8$, $COR^{14}$ or $(C_1-C_6)$alkyl $R^5$, $R^6$=independently of one another H, F, Cl, $(C_1-C_6)$alkyl, $CF_3$ or $OCF_3$ $R^7$=H, $C(=O)$—$Y(-CH_2)_k$—Y—$C(=O)R^9$ or $C(=O)$—$Y(-CH_2)_k$—$NHR^{10}$ k=2 to 16

Y=single bond or $NR^{13}$ $R^8$=H, $(C_1-C_6)$alkyl, or $(C_3-C_7)$cycloalkyl $R^9$=OH or $NHCH_2[-CH(OH)]_m$—$CH_2OH$ or a form thereof protected in a suitable way $R^{10}$=H, $C(=O)[-CH(OH)]_m$—$CH_2OH$ or a form thereof protected in a suitable way m=0 to 5

$R^{11}$=H, $(C_1-C_6)$alkyl, $(C_3-C_7)$cycloalkyl, (substituted) phenyl or $OR^{12}$ $R^{12}$=$(C_1-C_6)$alkyl or $(C_3-C_7)$cycloalkyl $R^{13}$=$(C_1-C_6)$alkyl or $(C_3-C_7)$cycloalkyl, aryl or heteroaryl $R^{14}$=OH, $OR^{12}$, $NR^{13}(-CH_2)_n$—Y—$C(=O)R^9$ or $NR^{13}(-CH_2)_n$—$NHR^{10}$ in the presence of a silylating agent and of a cyclization catalyst.

The process of the invention then comprises cyclizing compounds of the general formula (IV)

(IV)

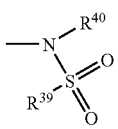

in which the symbols, substituents and indices—where not defined above—have the following meaning, X'=X, $CHOSi(alkyl)_o(aryl)_p$ with o, p=1 to 3 and o+p=3, $C(Oalkyl)_2$ or cyclic ketal such as $C[O-(CH_2)_q-O]$ with q=2, 3

$R^{1'}$, $R^{2'}$=$R^1$, $R^2$ and O-protective group $R^{3'}$, $R^{4'}$=$R^3$, $R^4$, $CH_2NHCO_2CH_2(C_6H_5)$, $CH_2N[Si(alkyl)_o(aryl)_p]$—$CO_2CH_2(C_6H_5)$, $CH_2NHCO_2$-tert.Bu, $CH_2N[Si(alkyl)_o$-(phenyl)$_p]CO_2$-tert.Bu, $CH_2NHC(C_6H_5)_3$, $CH_2N=C(C_6H_5)_2$ or $CH_2N=CH[C_6H_4(R^6)]$

-B=

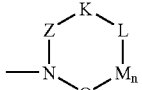 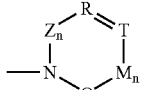 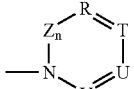

or -B=

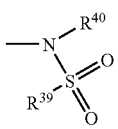

to give (precursor) products of the general formula (V), which can be deprotected to give the compound (I)

(V)

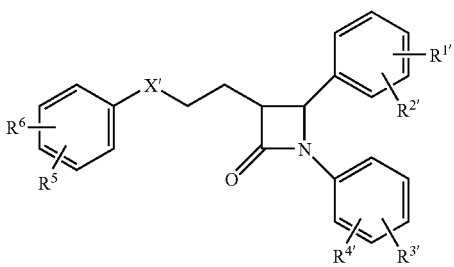

where the cyclization catalyst is represented by one of the general formulae below (XII)

as cation, where $R^{16}$, $R^{17}$, $R^{18}$, $R^{19}$ are independently of one another aryl, $(C_1-C_{15})$alkyl—especially $(C_1-C_{10})$alkyl-, benzyl-, especially butyl, $R^{41}$ is aryl, $(C_1-C_{15})$alkyl—especially $(C_1-C_{10})$alkyl-, benzyl, $R^{42}$ is $(C_1-C_{15})$alkyl—especially $(C_1-C_{10})$alkyl-, benzyl, $(C_5-C_8)$cycloalkyl, aryl, where aryl may be substituted by F, Cl, Br, I, —OH, —$O(C_1-C_3)$alkyl, —$NH_2$, —$NH(C_1-C_3)$alkyl, —$N[(C_1-C_3)$alkyl$]_2$, —C(O)OH, —$C(O)O(C_1-C_3)$alkyl, —$C(O)NH_2$, —$C(O)NH(C_1-C_3)$alkyl, —$C(O)N[(C_1-C_3)$alkyl$]_2$, —$SO_2NH_2$, —$SO_2NH(C_1-C_3)$alkyl, —$SO_2N[(C_1-C_3)$alkyl$]_2$, —CN, $(C_1-C_{12})$alkyl and $(C_5-C_8)$cycloalkyl, and (VIII)

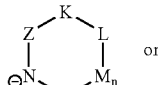 or

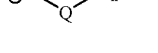

-continued

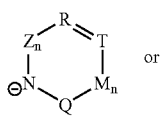
(IX)

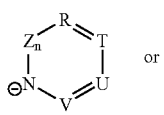
(X)

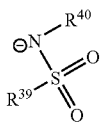
(XI)

as anion.

or where the cation in this cyclization catalyst corresponds to that of the general formula (XII), and the anion is $R^{41}O^{-1}$, or where the cation in this cyclization catalyst corresponds to that of the general formula (XII), and the anion is $R^{42}COO^-$ or where the cation in this cyclization catalyst corresponds to the general formula (XII), and the anion is $Cl^{-1}$, $Br^-$ or $I^-$, and these are combined with $Ag_2O$.

In a particularly preferred embodiment, the process of the invention comprises reacting compounds of the general formula (II)

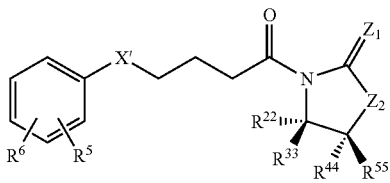
(II)

with imines of the general formula (III)

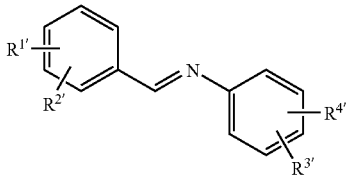
(III)

to give intermediates of the general formula (IV'),

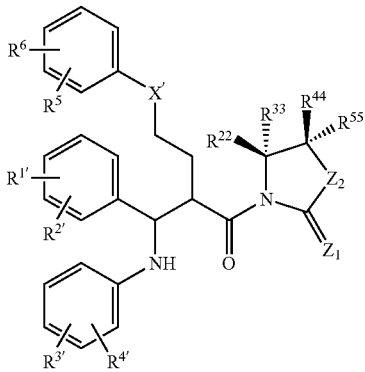
(IV')

which are then cyclized to give (precursor) products of the general formula (V) which can be deprotected to give a compound (I),

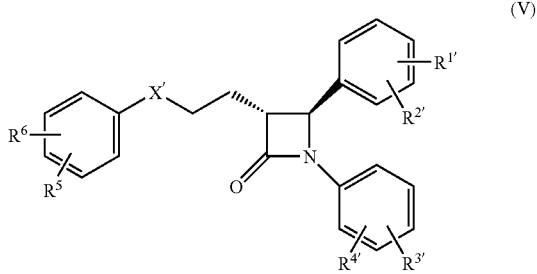
(V)

in which the symbols, substituents and indices—where not defined above—have the following meaning, $X'=X$, QHOSi(alkyl)$_o$(aryl)$_p$ with o, p=1 to 3 and o+p=3, C(Oalkyl)$_2$ or cyclic ketal such as C[O(—CH$_2$)$_q$—O] with q=2, 3

$R^{22}$, $R^{33}$, $R^{44}$, $R^{55}$=independently of one another H, aryl or (C$_1$-C$_{10}$)alkyl $Z_1$, $Z_2$=independently of one another O, NH, NR$^{15}$, or S $R^{15}$=aryl or (C$_1$-C$_{10}$)alkyl, $R^{1'}$, $R^{2'}$=$R^1$, $R^2$ and O-protective group $R^{3'}$, $R^{4'}$=$R^3$, $R^4$, CH$_2$NHCO$_2$CH$_2$(C$_6$H$_5$), CH$_2$N[Si(alkyl)$_o$(aryl)$_p$]—CO$_2$CH$_2$(C$_6$H$_5$), CH$_2$NHCO$_2$-tert.Bu, CH$_2$N[Si(alkyl)$_o$-(phenyl)$_p$]CO$_2$-tert.Bu, CH$_2$NHC(C$_6$H$_5$)$_3$, CH$_2$N=C(C$_6$H$_5$)$_2$ or CH$_2$N=CH[C$_6$H$_4$(R$^6$)]

where the cyclization catalyst is represented by one of the general formulae (VIa) to (VII)

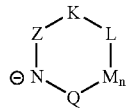 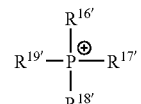
(VIa)

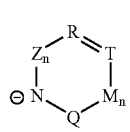 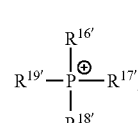
(VIb)

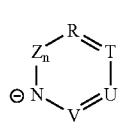 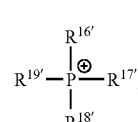
(VIc)

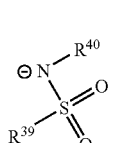 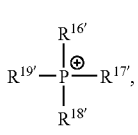
(VII)

in this case, $R^{16'}$, $R^{17'}$, $R^{18'}$, $R^{19'}$ are independently of one another aryl, (C$_1$-C$_{15}$)alkyl.

In a further particularly preferred embodiment, the process of the invention comprises reacting compounds of the general formula (II)

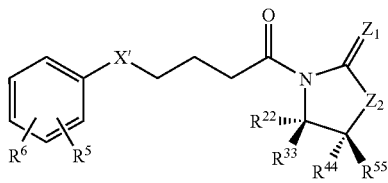

with imines of the general formula (III)

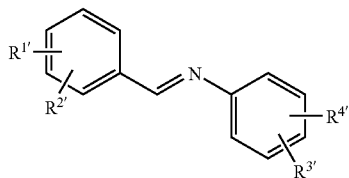

to give intermediates of the general formula (IV'),

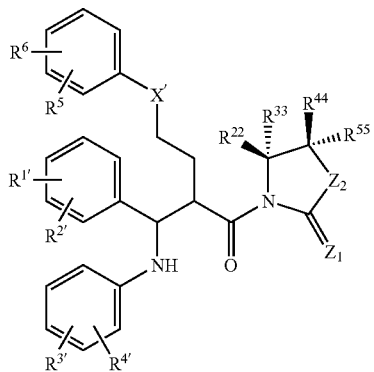

which are then cyclized to give (precursor) products of the general formula (V) which can be deprotected to give a compound (I),

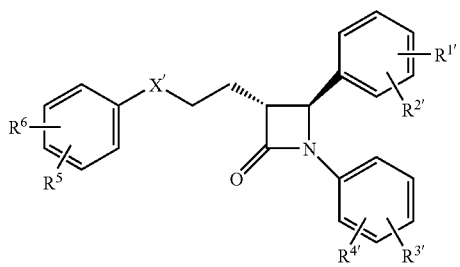

in which the symbols, substituents and indices—where not defined above—have the following meaning, X'=X, CHOSi(alkyl)$_o$(aryl)$_p$ with o, p=1 to 3 and o+p =3, C(Oalkyl)$_2$ or cyclic ketal such as C[O(—CH$_2$)$_q$—O] with q=2, 3

$R^{22}$, $R^{33}$, $R^{44}$, $R^{55}$=independently of one another H, aryl or (C$_1$-C$_{10}$)alkyl $Z_1$, $Z_2$=independently of one another O, NH, NR$^{15}$, or S $R^{15}$=aryl or (C$_1$-C$_{10}$)alkyl, $R^{1'}$, $R^{2'}$=$R^1$, $R^2$ and O-protective group $R^{3'}$, $R^{4'}$=$R^3$, $R^4$, CH$_2$NHCO$_2$CH$_2$(C$_6$H$_5$), CH$_2$N[Si(alkyl)$_o$(aryl)$_p$]—CO$_2$CH$_2$(C$_6$H$_5$), CH$_2$NHCO$_2$-tert.Bu, CH$_2$N[Si(alkyl)$_o$-(phenyl)$_p$]CO$_2$-tert.Bu, CH$_2$NHC(C$_6$H$_5$)$_3$, CH$_2$N═C(C$_6$H$_5$)$_2$ or CH$_2$N═CH[C$_6$H$_4$(R$^6$)]

where the cation in the cyclization catalyst corresponds to that of the general formula (XII), and the anion is $R^{41}O^-$.

In a further particularly preferred embodiment, the process of the invention comprises reacting compounds of the general formula (II)

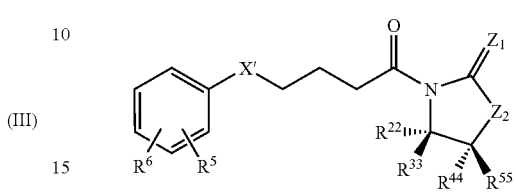

with imines of the general formula (III)

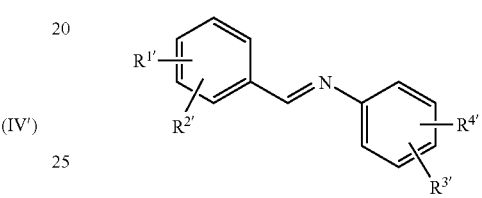

to give intermediates of the general formula (IV'),

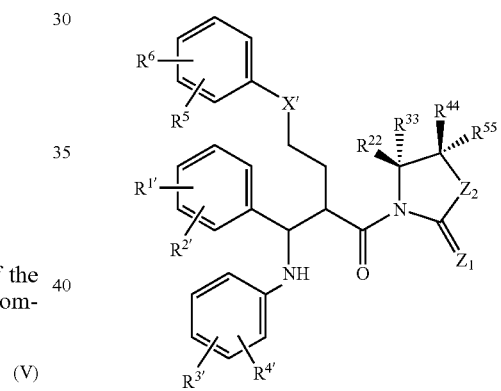

which are then cyclized to give (precursor) products of the general formula (V) which can be deprotected to give a compound (I),

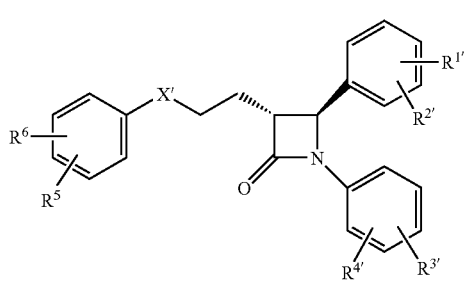

in which the symbols, substituents and indices—where not defined above—have the following meaning, X'=X, CHOSi(alkyl)$_o$(aryl)$_p$ with o, p=1 to 3 and o+p =3, C(Oalkyl)$_2$ or cyclic ketal such as C[O(—CH$_2$)$_q$—O] with q=2, 3

$R^{22}$, $R^{33}$, $R^{44}$, $R^{55}$=independently of one another H, aryl or ($C_1$-$C_{10}$)alkyl $Z_1$, $Z_2$=independently of one another O, NH, $NR^{15}$, or S $R^{15}$=aryl or ($C_1$-$C_{10}$)alkyl, $R^{1'},R^{2'}=R^1, R^2$ and O-protective group $R^{3'}$, $R^{4'}=R^3$, $R^4$, $CH_2NHCO_2CH_2(C_6H_5)$, $CH_2N[Si(alkyl)_o (aryl)_p]$—$CO_2CH_2(C_6H_5)$, $CH_2NHCO_2$-tert.Bu, $CH_2N[Si(alkyl)_o$-$(phenyl)_p]CO_2$-tert.Bu, $CH_2NHC(C_6H_5)_3$, $CH_2N=C(C_6H_5)_2$ or $CH_2N=CH[C_6H_4(R^6)]$ where the cation in the cyclization catalyst corresponds to that of the general formula (XII), and the anion is $R^{42}COO^-$.

Particularly preferred cyclization catalysts have an anion which is derived from
oxazolidin-2-one
4-benzyloxazolidin-2-one
4-phenyloxazolidin-2-one
4-isopropyloxazolidin-2-one
4-tert-butyloxazolidin-2-one
4-isopropyl-5,5-dimethyloxazolidin-2-one
4-benzyl-5,5-dimethyloxazolidin-2-one
4-phenyl-5,5-dimethyloxazolidin-2-one
4-isopropyl-5,5-dimethyloxazolidin-2-one
4-tert-butyl-5,5-dimethyloxazolidin-2-one
4-methyl-5-phenyloxazolidin-2-one
cis-4,5-diphenyloxazolodin-2-one
4-isopropyl-5,5-diphenyloxazolidin-2-one
1-methyl-4-methyleneimidazolidin-2-one
imidazole
phthalimide
2,10-camphorsultam
1-phenyl-3-pyrazolidinone,
or which is an alkoxide
or which is a carboxylate in combination with tetraethylphosphonium, tetrabutylphosphonium or tetraoctylphosphonium as cation.

The diphenylazetidinone compounds which can be prepared according to the invention are frequently employed in practice as pharmaceutically acceptable salts since these are particularly suitable for medical applications because of their greater solubility in water compared with the starting or basic compounds. These salts must have a pharmaceutically acceptable anion or cation. Suitable pharmaceutically acceptable acid addition salts of the compounds which can be prepared according to the invention are salts of inorganic acids such as hydrochloric acid, hydrobromic, phosphoric, metaphosphoric, nitric, sulfonic and sulfuric acid and of organic acids such as, for example, acetic acid, benzenesulfonic, benzoic, citric, ethanesulfonic, fumaric, gluconic, glycolic, isothionic, lactic, lactobionic, maleic, malic, methanesulfonic, succinic, p-toluenesulfonic, tartaric and trifluoroacetic acids. The chlorine salt is particularly preferably used for medical purposes. Suitable pharmaceutically acceptable basic salts are ammonium salts, alkali metal salts (such as sodium and potassium salts) and alkaline earth metal salts (such as magnesium and calcium salts).

The compounds of the general formula (I) and their pharmaceutically acceptable salts and physiologically functional derivatives represent ideal medicaments for the treatment of lipid metabolism disorders, especially of hyperlipidemia. The compounds of the general formula (I) are likewise suitable for influencing the serum cholesterol level and for the prevention and treatment of arteriosclerotic manifestations.

For further details concerning the compounds themselves, and for their processing, combination with other active ingredients etc., express reference is made to WO 02/50027

The following table lists typical examples of the radical -B of the general formula (IV) or in anionic form for the general formulae (VIII) to (XI), where the "H" on the "HN" in the ring or on the molecule in each case in the tables is superfluous in order to afford the radical -B or the relevant anion $B^{\ominus}$.

Examples of H-B or $H^{\oplus}B^{\ominus}$ in the general formulae (II), (IV) and (VIII) to (XI) are

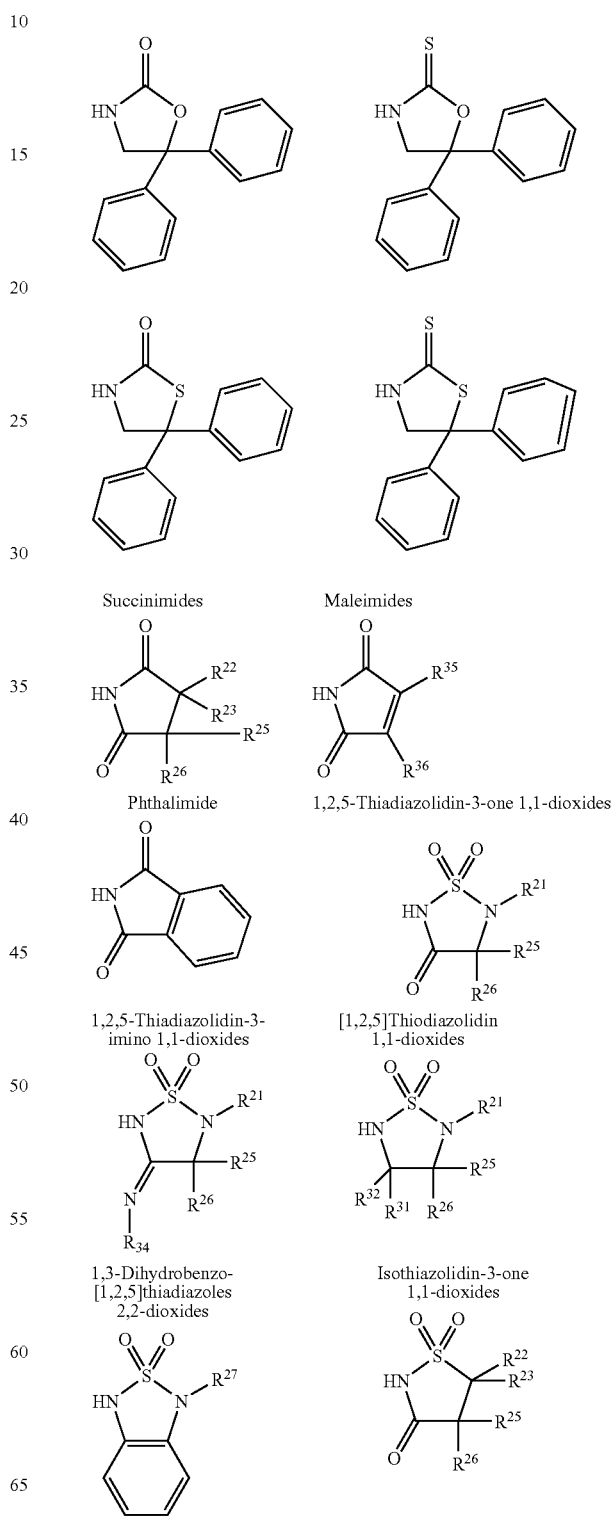

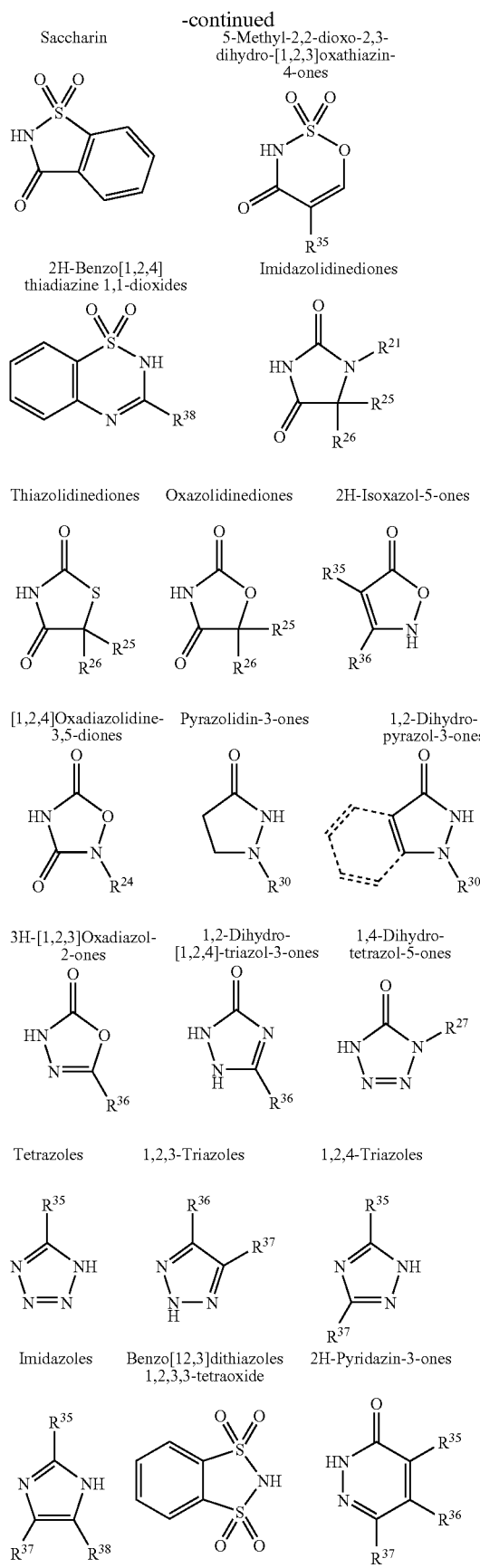
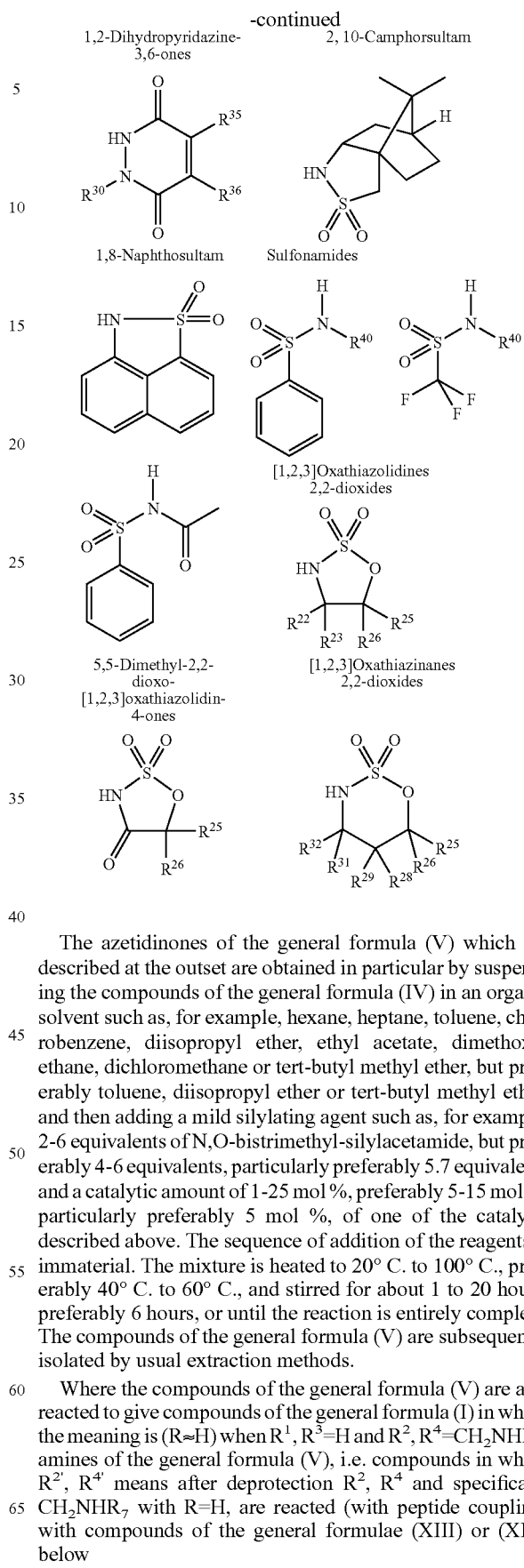

The azetidinones of the general formula (V) which are described at the outset are obtained in particular by suspending the compounds of the general formula (IV) in an organic solvent such as, for example, hexane, heptane, toluene, chlorobenzene, diisopropyl ether, ethyl acetate, dimethoxyethane, dichloromethane or tert-butyl methyl ether, but preferably toluene, diisopropyl ether or tert-butyl methyl ether, and then adding a mild silylating agent such as, for example, 2-6 equivalents of N,O-bistrimethyl-silylacetamide, but preferably 4-6 equivalents, particularly preferably 5.7 equivalents and a catalytic amount of 1-25 mol %, preferably 5-15 mol %, particularly preferably 5 mol %, of one of the catalysts described above. The sequence of addition of the reagents is immaterial. The mixture is heated to 20° C. to 100° C., preferably 40° C. to 60° C., and stirred for about 1 to 20 hours, preferably 6 hours, or until the reaction is entirely complete. The compounds of the general formula (V) are subsequently isolated by usual extraction methods.

Where the compounds of the general formula (V) are also reacted to give compounds of the general formula (I) in which the meaning is (R≈H) when $R^1$, $R^3$=H and $R^2$, $R^4$=$CH_2NHR_7$, amines of the general formula (V), i.e. compounds in which $R^{2'}$, $R^{4'}$ means after deprotection $R^2$, $R^4$ and specifically $CH_2NHR_7$ with R=H, are reacted (with peptide coupling) with compounds of the general formulae (XIII) or (XIV) below

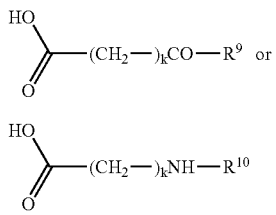

to give the desired compounds after preceding elimination of protective groups. Other compounds of the general formula (I) are formed by simple deprotection of the corresponding compounds of the general formula (V) without further reactions.

For detailed characterization of the process conditions, reference is made to the following examples and the prior art cited in the introduction, which also applies to the silylating agents normally employed.

The invention is explained in detail in the following examples.

EXAMPLES

Example 1

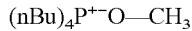

Tetrabutylphosphonium Methoxide

Potassium methoxylate (475.5 mg) is suspended in methanol (7 ml) at room temperature under an argon atmosphere. A methanolic solution (3 ml) of tetrabutylphosphonium chloride (2 g) is added thereto. The mixture is stirred at room temperature for 2 hours and filtered under argon through a syringe filter, and the solvent is removed. The residue is weighed and taken up in tetrahydrofuran (THF) (5 ml). A 1.35 molar solution of tetrabutylphosphonium methoxide is obtained.

Example 2

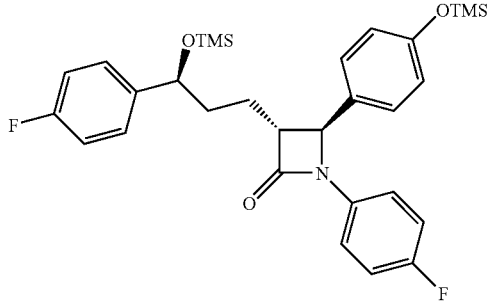

Cyclization of 3-{5-(4-Fluorophenyl)-2-[(4-fluorophenylamino)-(4-trimethylsilanyloxyphenyl)methyl]-5-trimethylsilanyloxypentanoyl}-4-phenyloxazolidin-2-one with the compound from Example 1

3-{5-(4-Fluorophenyl)-2-[(4-fluorophenylamino)-(4-trimethylsilanyloxy-phenyl)methyl]-5-trimethylsilanyloxypentanoyl}-4-phenyloxazolidin-2-one (10 mg) is suspended in methyl t-butyl ether (MTB ether) (1 ml) under argon while cooling in ice. N,O-Bistrimethylsilylacteamide (20.75 µl) is added, followed by tetrabutylphosphonium methoxide (20.65 µl; 1.35 M in THF). The mixture is stirred at room temperature for one hour. Reaction to give 1-(4-fluorophenyl)-3-[3-(4-fluorophenyl)-3-trimethylsilanyloxypropyl]-4-(4-trimethylsilanyloxyphenyl)azetidin-2-one is found by means of thin-layer chromatography and LC/MS comparison (liquid chromatography/mass spectrometry) (M+H,-TMS,-HOTMS: 392).

Example 3

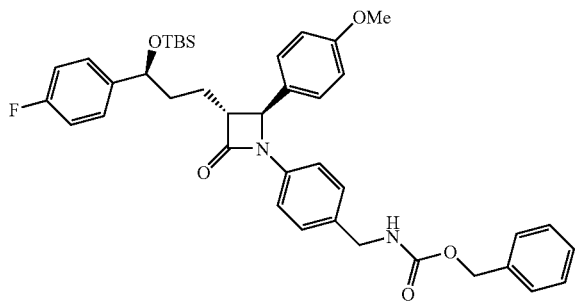

Cyclization of benzyl {4-[5-(tert-butyidimethylsilanyloxy)-5-(4-fluoro-phenyl)-1-(4-methoxyphenyl)-2-(2-oxo-4-phenyloxazolidine-3-carbonyl)pentylamino]benzyl}carbamylate with the compound from Example 1

Benzyl {4-[5-(tert-butyidimethylsilanyloxy)-5-(4-fluorophenyl)-1-(4-methoxy-phenyl)-2-(2-oxo-4-phenyloxazolidine-3-carbonyl)pentylamino]benzyl}carbamylate (10 mg) is suspended in MTB ether (1 ml) while cooling in ice and in an argon atmosphere. N,O-Bistrimethylsilylacteamide (17.5 µl) is added, followed by tetrabutylphosphonium methoxide (23.6 µl; 1 M in THF). The mixture is stirred at room temperature for two hours. The reaction is quenched with water, and the aqueous phase is extracted with ethyl acetate. Reaction to give benzyl {4-[3-[3-(tert-butyldimethylsilanyloxy)-3-(4-fluorophenyl)propyl]-2-(4-methoxyphenyl)-4-oxoazetidin-1-yl]benzyl}carbamylate is found by means of thin-layer chromatography and LC/MS comparison. $^1$H-NMR ($d^6$-DMSO) −0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 4

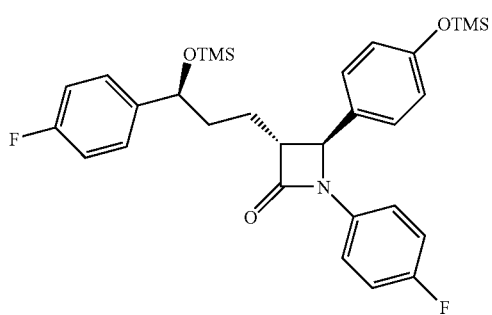

Cyclization of 3-{5-(4-fluorophenyl)-2-[(4-fluorophenylamino)-(4-trimethylsilanyloxyphenyl)methyl]-5-trimethylsilanyloxypentanoyl}-4-phenyloxazolidin-2-one with tetrabutylphosphonium chloride and silver(I) oxide 3-{5-(4-Fluorophenyl)-2-[(4-fluorophenylamino)-(4-trimethylsilanyloxy-phenyl)methyl]-5-trimethylsilanyloxypentanoyl}-4-phenyloxazolidin-2-one (10 mg) is suspended in MTB ether (1 ml) under argon while cooling in ice. N,O-Bistrimethylsilylacteamide (20.75 µl) is added, followed by tetrabutylphosphonium chloride (4.2 mg) and silver(I) oxide (3.2 mg). The mixture is stirred at room temperature. A reaction to give 1-(4-fluorophenyl)-3-[3-(4-fluorophenyl)-3-trimethylsilanyloxypropyl]-4-(4-trimethylsilanyloxyphenyl)azetidin-2-one is found by means of thin-layer chromatography and LC/MS comparison (M+H,-TMS,-HOTMS: 392).

Example 5

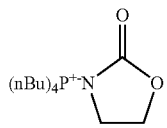

Tetrabutylphosphonium oxazolidin-2-one

Tetrabutylphosphonium chloride (300 mg) is dissolved in methanol (3 ml), and silver(I) oxide (203.85 mg) is added. The mixture is stirred at room temperature under argon for 16 hours. The reaction solution is filtered through a syringe filter. Oxazolidin-2-one (104.4 mg) is added to the filtrate and stirred at room temperature for 2 hours. The solvent is removed in a rotary evaporator. Tetrabutylphosphonium oxazolidin-2-one (200 mg) is obtained as colorless oil. $^1$H-NMR (d$^6$-DMSO) 0.9 (m, 12 H), 1.4 (m, 16 H), 2.2 (m, 8 H), 3.4 (t, 2 H), 3.85 (t, 2 H).

Example 6

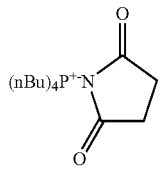

Tetrabutylphosphonium Succinimide

The compound is prepared from succinimide in analogy to the method in Example 5. $^1$H-NMR (d$^8$-THF) 0.95 (m, 12 H), 1.4-1.6 (m, 16 H), 2.3 (s, 4 H), 2.55 (m, 8 H).

Example 7

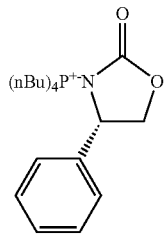

Tetrabutylphosphonium 4-phenyloxazolidin-2-one

The compound is prepared from 4-phenyloxazolidin-2-one in analogy to the method in Example 5. $^1$H-NMR (d$^6$-DMSO) 0.9 (m, 12 H), 1.4 (m, 16 H), 2.2 (m, 8 H), 3.6 (t, 1 H), 4.35 (t, 1 H), 4.75 (m, 1 H), 7.2-7.3 (m, 5 H).

Example 8

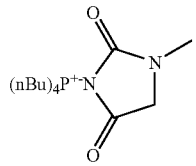

Tetrabutylphosphonium 1-methylimidazolidine-2,4-dione

The compound is prepared from 1-methylimidazolidine-2,4-dione in analogy to the method in Example 5. $^1$H-NMR (d$^6$-DMSO) 0.9 (m, 12 H), 1.44 (m, 16 H), 2.15 (m, 8 H), 2.65 (s, 3 H), 3.13 (s, 2 H).

Example 9

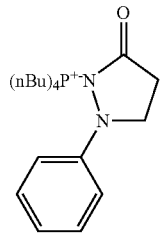

Tetrabutylphosphonium 1-phenylpyrazolidin-3-one

The compound is prepared from 1-phenylpyrazolidin-3-one in analogy to the method in Example 5. $^1$H-NMR (d$^6$-DMSO) 0.9 (t, 12 H), 1.4 (m, 17 H), 1.55 (m, 1 H), 2.2 (m, 8 H), 5.5 (bs, 1 H), 6.95 (t, 1 H), 7.28 (t, 2 H), 7.53 (d, 2 H), 7.9 (s, 1 H).

Example 10

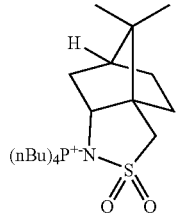

Tetrabutylphosphonium 10,10-dimethyl-3-thia-4-azatricyclo-[5.2.1.01,5]decane 3,3-dioxide The compound is prepared from 2,10-camphorsultam in analogy to the method in Example 5. $^1$H-NMR (d$^6$-DMSO) 0.75 (s, 3 H), 0.9 (t, 12 H), 1.0 (s, 3 H), 1.1-1.25 (m, 2 H), 1.4 (m, 16 H), 1.5-1.8 (m, 4 H), 2.2 (m, 8 H), 2.5 (m, 2 H), 3.05 (m, 1 H), 3.15 (d, 1 H).

Example 11

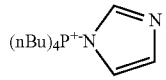

Tetrabutylphosphonium imidazolide

The compound is prepared from imidazole in analogy to the method in Example 5. $^1$H-NMR (d$^6$-DMSO) 0.9 (t, 12 H), 1.4 (m, 16 H), 2.2 (m, 8 H), 6.7 (s, 2 H), 7.15 (s, 1 H).

Example 12

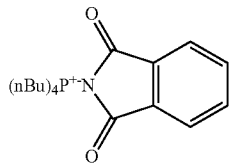

Tetrabutylphosphonium phthalimide

The compound is prepared from phthalimide in analogy to the method in Example 5. $^1$H-NMR (d$^6$-DMSO) 0.9 (t, 12 H), 1.4 (m, 16 H), 2.2 (m, 8 H), 7.38 (m, 2 H), 7.42 (m, 2 H).

Example 13

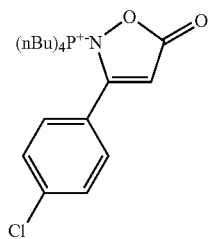

Tetrabutylphosphonium 3-(4-chlorophenyl)-2H-isoxazol-5-one

The compound is prepared from 3-(4-chlorophenyl)-2H-isoxazol-5-one in analogy to the method in Example 5. $^1$H-NMR (d$^6$-DMSO) 0.9 (t, 12 H), 1.4 (m, 16 H), 2.2 (m, 8 H), 4.3 (bs, 1 H), 7.35 (m, 2 H), 7.55 (m, 2 H).

Example 14

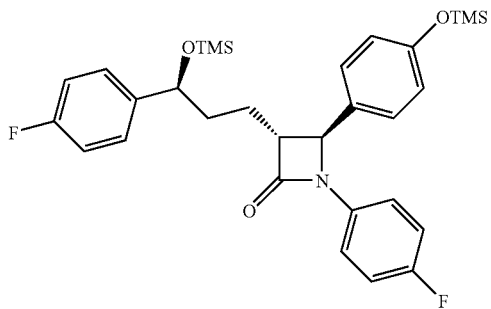

Cyclization of 3-{5-(4-fluorophenyl)-2-[(4-fluorophenylamino)-(4-trimethylsilanyloxyphenyl)methyl]-5-trimethylsilanyloxypentanoyl}4-phenyloxazolidin-2-one with the compound from Example 5

3-{5-(4-Fluorophenyl)-2-[(4-fluorophenylamino)-(4-trimethylsilanyloxy-phenyl)methyl]-5-trimethylsilanyloxypentanoyl}-4-phenyloxazolidin-2-one (10 mg) is suspended in MTB ether (1 ml) under argon while cooling in ice. N,O-Bistrimethylsilylacteamide (20.75 µl) is added, followed by a catalytic amount of tetrabutylphosphonium oxazolidin-2-one (3 mg) dissolved in MTB ether (100 µl). The mixture is stirred at room temperature for 1 hour. Reaction to give 1-(4-fluorophenyl)-3-[3-(4-fluorophenyl)-3-trimethylsilanyloxypropyl]-4-(4-trimethylsilanyloxyphenyl)azetidin-2-one is found by means of thin-layer chromatography and LC/MS comparison (M+H,-TMS,-HOTMS: 392).

Example 15

Cyclization of 3-{5-(4-fluorophenyl)-2-[(4-fluorophenylamino)-(4-trimethyl-silanyloxyphenyl)methyl]-5-trimethylsilanyloxypentanoyl}-4-phenyloxazol-idin-2-one to 1-(4-fluorophenyl)-3-[3-(4-fluorophenyl)-3-trimethylsilanyloxypropyl]-4-(4-trimethylsilanyloxyphenyl)azetidin-2-one is carried out in an analogous manner to the method in Example 14, but with tetrabutylphosphonium succinimide from Example 6 as cyclization catalyst. The spectroscopic data agree with those of the product from Example 10 (M+H,-TMS,-HOTMS: 392).

Example 16

Cyclization of 3-{5-(4-fluorophenyl)-2-[(4-fluorophenylamino)-(4-trimethyl-silanyloxyphenyl)methyl]-5-trimethylsilanyloxypentanoyl}-4-phenyloxazol-idin-2-one to 1-(4-fluorophenyl)-3-[3-(4-fluorophenyl)-3-trimethylsilanyloxypropyl]-4-(4-trimethylsilanyloxyphenyl)azetidin-2-one is carried out in an analogous manner to the method in Example 14, but with tetrabutylphosphonium 4-phenyloxazolidin-2-one from Example 7 as cyclization catalyst. The spectroscopic data agree with those of the product from Example 10 (M+H,-TMS,-HOTMS: 392).

Example 17

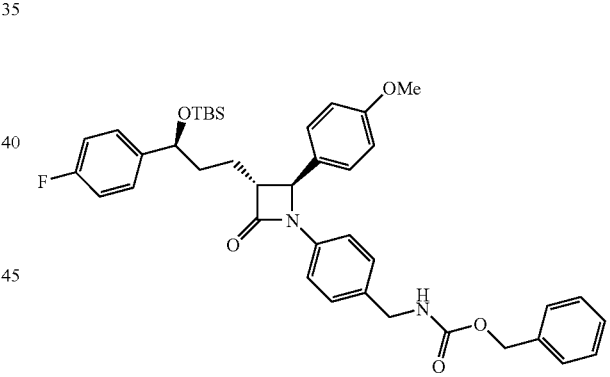

Cyclization of benzyl {4-[5-(tert-butyidimethylsilanyloxy)-5-(4-fluorophenyl)-1-(4-methoxyphenyl)-2-(2-oxo-4-phenyloxazolidine-3-carbonyl)pentylamino]benzyl}carbamylate with the compound from Example 5

Benzyl {4-[5-(tert-butyidimethylsilanyloxy)-5-(4-fluorophenyl)-1-(4-methoxyphenyl)-2-(2-oxo-4-phenyloxazolidine-3-carbonyl)-pentylamino]benzyl}carbamylate (500 mg) is suspended in MTB ether (6 ml) while cooling in ice and in an argon atmosphere. N,O-Bistrimethylsilylacteamide (1.0 ml) is added, followed by tetrabutylphosphonium oxazolidin-2-one (40.8 mg) dissolved in MTB ether (1 ml). The mixture is stirred at room temperature for two hours. This is followed by addition of a 1N aqueous hydrogen chloride solution (HCl$_{(aq)}$) (1 ml), while cooling in ice methanol (1 ml)

and tetrahydrofuran (2 ml). The mixture is stirred at room temperature overnight. The reaction solution is concentrated and taken up in ethyl acetate. The organic phase is washed successively with 2N HCl$_{(aq)}$, saturated sodium bicarbonate solution and saturated brine. It is then dried over sodium sulfate and filtered, and the solvent is removed in a rotary evaporator. Purification by chromatography (1:6 ethyl acetate/n-heptane) on an SiO$_2$ cartridge (5 g) results in benzyl {4-[3-[3-(tert-butyodimethylsilanyloxy)-3-(4-fluorophenyl)propyl]-2-(4-methoxyphenyl)-4-oxoazetidin-1-yl]benzyl}carbamylate (240 mg) $^1$H -NMR. (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 18

Cyclization of benzyl {4-[5-(tert-butyidimethylsilanyloxy)-5-(4-fluorophenyl)-1-(4-methoxyphenyl)-2-(2-oxo-4-phenyloxazolidine-3-carbonyl)pentyl-amino]benzyl}carbamylate to {4-[3-[3-(tert-butyidimethylsilanyloxy)-3-(4-fluorophenyl)propyl]-2-(4-methoxyphenyl)-4-oxoazetidin-1-yl]benzyl}carbamylate is carried out in an analogous manner to the method in Example 17, but with tetrabutylphosphonium 1-methylimidazolidine-2,4-dione from Example 8 as cyclization catalyst. The spectroscopic data agree with those of the product from Example 17: $^1$H-NMR (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 19

Cyclization of benzyl {4-[5-(tert-butyldimethylsilanyloxy)-5-(4-fluorophenyl)-1-(4-methoxyphenyl)-2-(2-oxo-4-phenyloxazolidine-3-carbonyl)pentyl-amino]benzyl}carbamylate to {4-[3-[3-(tert-butyldimethylsilanyloxy)-3-(4-fluorophenyl)propyl]-2-(4-methoxyphenyl)-4-oxoazetidin-1-yl]benzyl}carbamylate is carried out in an analogous manner to the method in Example 17, but with tetrabutylphosphonium 1-phenylpyrazolidin-3-one from Example 9 as cyclization catalyst. The spectroscopic data agree with those of the product from Example 17: $^1$H-NMR (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 20

Cyclization of benzyl {4-[5-(tert-butyidimethylsilanyloxy)-5-(4-fluorophenyl)-1-(4-methoxyphenyl)-2-(2-oxo-4-phenyloxazolidine-3-carbonyl)pentyl-amino]benzyl}carbamylate to {4-[3-[3-(tert-butyldimethylsilanyloxy)-3-(4-fluorophenyl)propyl]-2-(4-methoxyphenyl)-4-oxoazetidin-1-yl]benzyl}carbamylate is carried out in an analogous manner to the method in Example 17, but with tetrabutylphosphonium 10,10-dimethyl-3-thia-4-azatricyclo[5.2.1.0$^{1,5}$]decane 3,3-dioxide from Example 10 as cyclization catalyst. The spectroscopic data agree with those of the product from Example 17: $^1$H-NMR (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 21

Cyclization of benzyl {4-[5-(tert-butyldimethylsilanyloxy)-5-(4-fluorophenyl)-1-(4-methoxyphenyl)-2-(2-oxo-4-phenyloxazolidine-3-carbonyl)pentyl-amino]benzyl}carbamylate to {4-[3-[3-(tert-butyldimethylsilanyloxy)-3-(4-fluorophenyl)propyl]-2-(4-methoxyphenyl)-4-oxoazetidin-1-yl]benzyl}carbamylate is carried out in an analogous manner to the method in Example 17, but with tetrabutylphosphonium imidazolidide from Example 11 as cyclization catalyst. The spectroscopic data agree with those of the product from Example 17: $^1$H-NMR (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 22

Cyclization of benzyl {4-[5-(tert-butyidimethylsilanyloxy)-5-(4-fluorophenyl)-1-(4-methoxyphenyl)-2-(2-oxo-4-phenyloxazolidine-3-carbonyl)pentyl-amino]benzyl}carbamylate to {4-[3-[3-(tert-butyidimethylsilanyloxy)-3-(4-fluorophenyl)propyl]-2-(4-methoxyphenyl)-4-oxoazetidin-1-yl]benzyl}carbamylate is carried out in an analogous manner to the method in Example 17, but with tetrabutylphosphonium phthalimide from Example 12 as cyclization catalyst. The spectroscopic data agree with those of the product from Example 17: $^1$H-NMR (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 23

Cyclization of benzyl {4-[5-(tert-butyidimethylsilanyloxy)-5-(4-fluorophenyl)-1-(4-methoxyphenyl)-2-(2-oxo-4-phenyloxazolidine-3-carbonyl)pentyl-amino]benzyl}carbamylate to {4-[3-[3-(tert-butyldimethylsilanyloxy)-3-(4-fluorophenyl)propyl]-2-(4-methoxyphenyl)-4-oxoazetidin-1-yl]benzyl}carbamylate is carried out in an analogous manner to the method in Example 17, but with tetrabutylphosphonium 3-(4-chlorophenyl)-2H-isoxazol-5-one from Example 13 as cyclization catalyst. The spectroscopic data agree with those of the product from Example 17: $^1$H-NMR (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72,(m, 1 H), 4.82 (s, 1 H), 5.0 (s, 2 H), 6.9 (d, 2 H), 7.12 (m, 5 H), 7.35 (m, 10 H), 7.73 (t, 1 H).

Example 24

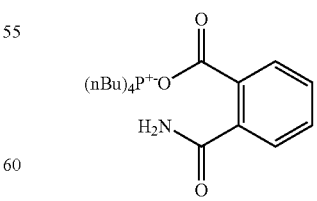

Tetrabutylphosphonium phthalamate

Tetrabutylphosphonium phthalamate is also prepared in the following way. A solution of tetrabutylphosphonium hydroxide (12.5 g; 40% in water) is prepared. Then phthalimide (2.7 g) is added, and the reaction solution is stirred at room temperature overnight. The water is then removed in a rotary evaporator, and the residue is taken up in toluene. The toluene is removed in a rotary evaporator, and the residue is again taken up in toluene. This procedure is repeated 4-5 times. The solvent is then removed to dryness. $^1$H-NMR (d$^6$-DMSO) 0.9 (t, 12 H), 1.42 (m, 16 H), 2.18 (m, 8 H), 7.05 (b, 1 H), 7.18 (m, 1 H), 7.29 (d, 2 H), 7.74 (d, 1 H), 10.35 (b, 1 H).

Example 25

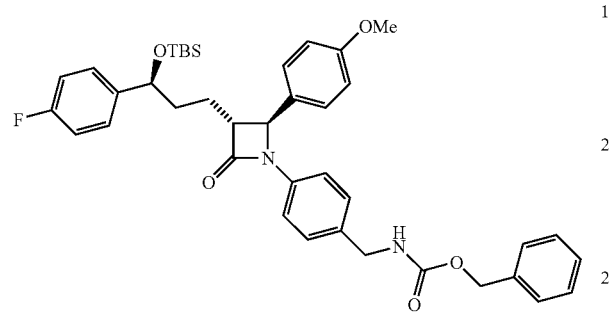

Cyclization of benzyl {4-[5-(tert-butyidimethylsilanyloxy)-5-(4-fluorophenyl)-1-(4-methoxyphenyl)-2-(2-oxo-4-phenyloxazolidine-3-carbonyl)pentylamino]benzyl}carbamylate with tetrabutylphosphonium phthalimide from Example 24

Benzyl {4-[5-(tert-butyldimethylsilanyloxy)-5-(4-fluorophenyl)-1-(4-methoxyphenyl)-2-(2-oxo-4-phenyloxazolidine-3-carbonyl)pentylamino]benzyl}-carbamylate (100 mg) is suspended in MTB ether (5 ml) while cooling in ice and in an argon atmosphere. N,O-Bistrimethylsilylacteamide (0.17 ml) is added, followed by tetrabutylphosphonium phthalimide (12 mg) dissolved in MTB ether (1 ml). The mixture is stirred at 50° C. for 2-3 hours. The reaction solution is concentrated and taken up in ethyl acetate. The organic phase is washed successively with 2N HCl$_{(aq)}$, saturated sodium bicarbonate solution and saturated brine. It is then dried over sodium sulfate and filtered, and the solvent is removed in a rotary evaporator. Purification by chromatography (Jones chromatography Flashmaster) results in benzyl {4-[3-[3-(tert-butyidimethylsilanyloxy)-3-(4-fluorophenyl) propyl]-2-(4-methoxyphenyl)-4-oxoazetidin-1-yl]benzyl}carbamylate (41 mg) $^1$H-NMR (d$^6$-DMSO) –0.18 (s, 3 H), 0.02 (s, 3 H), 0.85 (s, 9 H), 1.75 (bs, 4 H), 3.05 (bs, 1 H), 3.7 (s, 3 H), 4.1 (d, 2 H), 4.72 (m, 1 H), 4.82 (s, 1 H), 5.0 (s, 2 H), 6.9 (d, 2 H), 7.12 (m, 5 H), 7.35 (m, 10 H), 7.73 (t, 1 H).

Example 26

Cyclization of benzyl {4-[5-(tert-butyldimethylsilanyloxy)-5-(4-fluorophenyl)-1-(4-methoxyphenyl)-2-(2-oxo-4-phenyloxazolidine-3-carbonyl)pentyl-amino]benzyl}carbamylate with tetrabutylphosphonium phthalamate from Example 24 is carried out in an analogous manner to the method in Example 25, but in diisopropyl ether and at 50° C. within 6 hours. Reaction to give the analogous product from Example 25 is found by means of LC/MS comparison (liquid chromatography/mass spectrometry).

Example 27

Cyclization of benzyl {4-[5-(tert-butyidimethylsilanyloxy)-5-(4-fluorophenyl)-1-(4-methoxyphenyl)-2-(2-oxo4-phenyloxazolidine-3-carbonyl)pentyl-amino]benzyl}carbamylate with tetrabutylphosphonium phthalamate from Example 24 is carried out in an analogous manner to the method in Example 25, but in toluene and at 60° C. within 13 hours. Reaction to give the analogous product from Example 25 is found by means of LC/MS comparison (liquid chromatography/mass spectrometry).

Example 28

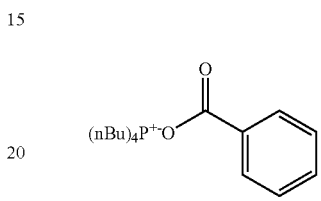

Tetrabutylphosphonium benzoate

Tetrabutylphosphonium benzoate is also prepared in the following way. A solution of tetrabutylphosphonium hydroxide (4.7 g; 40% in water) is prepared. Then benzoic acid (0.8 g) is added, and the reaction solution is stirred at room temperature for 5 hours. The water is then removed in a rotary evaporator, and the residue is taken up in toluene. The toluene is removed in a rotary evaporator, and the residue is again taken up in toluene. This procedure is repeated 4-5 times. The solvent is then removed to dryness.

Example 29

Cyclization of benzyl {4-[5-(tert-butyldimethylsilanyloxy)-5-(4-fluorophenyl)-1-(4-methoxyphenyl)-2-(2-oxo-4-phenyloxazolidine-3-carbonyl)pentyl-amino]benzyl}carbamylate with tetrabutylphosphonium benzoate from Example 28 is carried out in an analogous manner to the method in Example 25, but in diisopropyl ether and at 60° C. within 3 hours. Reaction to give the analogous product from Example 25 is found by means of LC/MS comparison (liquid chromatography/mass spectrometry).

Example 30

Cyclization of benzyl {4-[5-(tert-butyidimethylsilanyloxy)-5-(4-fluorophenyl)-1-(4-methoxyphenyl)-2-(2-oxo-4-phenyloxazolidine-3-carbonyl)pentyl-amino]benzyl}carbamylate with tetrabutylphosphonium acetate (commercial product was dried in vacuo) is carried out in an analogous manner to the method in Example 25, but in diisopropyl ether and at 60° C. within 0.5 hours. Reaction to give the analogous product from Example 25 is found by means of LC/MS comparison (liquid chromatography/mass spectrometry).

What is claimed is:

1. A process for the preparation of 1,4-diphenylazetidinone derivatives from β-substituted amino amides which are protected, said process comprising the reaction of said amides with one or more silylating agents and at least one cyclization catalyst consisting of a salt formed by the combination of a cation and an anion, said cation represented by the general formula:

$$R^{19}-\overset{R^{16}}{\underset{R^{18}}{P}}{}^{\oplus}-R^{17} \quad (XII)$$

wherein $R^{16}$, $R^{17}$, $R^{18}$ and $R^{19}$ are independently selected from the group consisting of aryl, $(C_1-C_{15})$alkyl and benzyl,
and said anion is represented by the formula:

$$\text{(VIII)}$$

or $$\text{(IX)}$$

or $$\text{(X)}$$

or $$\text{(XI)}$$

wherein:
Z=C=O, C=S, S=O, $SO_2$ or C=$NR^{20}$
K=O, S, $NR^{21}$ or $CR^{22}R^{23}$
L=$NR^{24}$ or $CR^{25}R^{26}$
n=0 or 1
M=O, C=O, $NR^{27}$ or $CR^{25}R^{29}$
Q=O, S, $NR^{30}$, $CR^{31}R^{32}$, C=O, C=S, S=O, $SO_2$ or C=$NR^{34}$
R=$CR^{35}$ or N
T=$CR^{36}$ or N
U=$CR^{37}$ or N
V=$CR^{38}$ or N
where $R^{20}$ to $R^{32}$ and $R^{34}$ to $R^{38}$ are independently selected from the group consisting of H, $(C_1-C_6)$alkyl, aryl or heteroaryl, wherein two alkyl radicals may together also form a cycloalkylene radical with a maximum of 6 carbons in the ring which may in turn be substituted by F, Cl, Br, I, $CF_3$, $NO_2$, $COO(C_1-C_6)$alkyl, $CON[(C_1-C_6)$alkyl$]_2$, cycloalkyl, $(C_1-C_{10})$alkyl, $(C_2-C_6)$alkenyl, O—$(C_1-C_6)$alkyl, O—CO—$(C_1-C_6)$alkyl, O—CO—$(C_1-C_6)$alkylene-aryl, $SO_2N[(C_1-C_6)$alkyl$]_2$, S-(C1-C6)alkyl, S—$(CH_2-)_n$aryl, SO—$(C_1-C_6)$alkyl, SO—$(CH_2-)_n$aryl, $SO_2$—$(C_1-C_6)$alkyl, $SO_2$-$(CH_2-)_n$aryl, $SO_2$—$N((C_1-C_6)$alkyl)$(CH_2)_n$aryl, or $SO_2$—$N((CH_2-)_n$aryl$)_2$, where n may be 0 to 6, and the aryl radical may be substituted up to twice by F, Cl, Br, $CF_3$, $SF_5$, $NO_2$, $OCF_3$, O—$(C_1-C_6)$alkyl or $(C_1-C_6)$alkyl; or by $N((C_1-C_6)$alkyl$)_2$, NH—CO—NH—$(C_1-C_6)$alkyl), NH—CO—NH-aryl, $N[(C_1-C_6)$alkyl]-CO—$(C_1-C_6)$alkyl, $N[(C_1-C_6)$alkyl]-COO—$(C_1-C_6)$alkyl, $N[(C_1-C_6)$alkyl]-CO-aryl, $N[(C_1-C_6)$alkyl]-COO-aryl, $N[(C_1-C_6)$alkyl]-CO—$N((C_1-C_6)$alkyl$)_2$, $N[(C_1-C_6)$alkyl]-CO—$N((C_1-C_6)$alkyl)-aryl, $N[(C_1-C_6)$alkyl]-CO—$N($aryl$)_2$, $N($aryl$)$-CO—$(C_1-C_6)$alkyl, $N($aryl$)$-COO—$(C_1-C_6)$alkyl, $N($aryl$)$-CO-aryl, $N($aryl$)$-COO-aryl, $N($aryl$)$-CO-$N((C_1-C_6)$alkyl$)_2$, $N($aryl$)$-CO—$N[(C_1-C_6)$alkyl]-aryl, $N($aryl$)$-CO—$N($aryl$)_2$, aryl, O—$(CH_2-)_n$aryl, where n may be 0 to 6, where the aryl radical may be substituted 1 to 3 times by F, Cl, Br, I, $OF_3$, $NO_2$, $OCF_3$, O—$(C_1-C_6)$alkyl, $(C_1-C_6)$alkyl, $N((C_1-C_6)$alkyl$)_2$, $SF_5$, $SO_2$—$CH_3$ or COO—$(C_1-C_6)$alkyl and where $R^{39}$ and $R^{40}$ are independently selected from the group consisting of $(C_1-C_6)$alkyl, with the stipulation that one or more non-adjacent carbon atoms may be replaced by NH or C=O, or are $(C_1-C_6)$ perfluoroalkyl, aryl or heteroaryl, or $R^{39}$ and $R^{40}$ together may form 1,8-naphthyl or 1,7,7-trimethylbicyclo[2.2.1]heptanyl and $R^{40}$ may also be H,
or where the cation component in this cyclization catalyst corresponds to the formula (XII), and the anion component is $R^{41}O^-$ or where the cation component in this cyclization catalyst corresponds to formula (XII) and the anion is $R^{42}COO^-$, or where the cation corresponds to formula (XII), and the anion is $Cl^-$, $Br^-$ or $I^-$, and
$R^{41}$ is aryl, $(C_1-C_{15})$alkyl, benzyl,
$R^{42}$ is selected from the group consisting of $(C_1-C_{15})$alkyl, benzyl, $(C_5-C_8)$cycloalkyl, aryl, where aryl may be substituted by F, Cl, Br, I, —OH, —O$(C_1-C_3)$alkyl, —$NH_2$, —$NH(C_1-C_3)$alkyl, —$N[(C_1-C_3)$alkyl$]_2$, —C(O)OH, —C(O)O$(C_1-C_3)$alkyl, —C(O)$NH_2$, —C(O)NH$(C_1-C_3)$alkyl, —C(O)$N[(C_1-C_3)$alkyl$]_2$, —$SO_2NH_2$, —$SO_2NH(C_1-C_3)$alkyl, —$SO_2N[(C_1-C_3)$alkyl$]_2$, —CN, $(C_1-C_{12})$alkyl and $(C_5-C_8)$cycloalkyl, followed by the reaction thereof with $Ag_2O$.

2. The process as recited in claim 1, wherein said 1,4-diphenylazetidinone derivatives are represented by the formula (I)

$$\text{(I)}$$

wherein:
X is selected from the group consisting of $CH_2$, CHOH, CO or $CHOCOR^{11}$
$R^1$ and $R^2$ are independently selected from the group consisting of H, OH, $OCF_3$, or O—$(C_1-C_6)$alkyl, O—$(C_3-C_7)$cycloalkyl, O—$COR^{11}$, CN, $CH_2NHR^7$, $CH_2NR^7R^8$, $NR^7R^5$, $COR^{14}$, F and Cl
$R^3$ and $R^4$ are independently selected from the group consisting of H, F, Cl, OH, $OCF_3$, O—$(C_1-C_6)$alkyl, O—$(C_3-C_7)$cycloalkyl, O—$COR^{11}$, CN, $CH_2NHR^7$, $CH_2NR^7R^5$, $NR^7R^8$, $COR^{14}$ and $(C_1-C_6)$alkyl
$R^5$ and $R^6$ are independently selected from the group consisting of H, F, Cl, $(C_1-C_6)$alkyl, $CF_3$ or $OCF_3$
$R^7$ is selected from the group consisting of H, O(=O)-Y(-$CH_2)_k$-Y-C(=O)$R^9$ or C(=O)-Y(-$CH_2)_k$-$NHR^{10}$
k is 2 to 16
Y is a single bond or $NR^{13}$ $R^8$ is H, $(C_1-C_6)$alkyl, or $(C_3-C_7)$cycloalkyl $R^9$ is OH or $NHCH_2[\text{—}CH(OH)]_m\text{—}CH_2OH$ $R^{10}$ is $H, C(\text{=}O)[\text{—}CH(OH)]_m\text{—}CH_2OH$ m is 0 to 5

$R^{11}$ is H, $(C_1-C_6)$alkyl, $(C_3-C_7)$cycloalkyl, (substituted) phenyl or $OR^{12}$ $R^{12}$ is $(C_1-C_6)$alkyl or $(C_3-C_7)$cycloalkyl $R^{13}$ is $(C_1-C_6)$alkyl or $(C_3-C_7)$cycloalkyl, aryl or heteroaryl, and $R^{14}$ is OH, $OR^{12}$, $NR^{13}(\text{—}CH_2)_n\text{-}Y\text{-}C(\text{=}O)R^9$ or $NR^{13}(\text{—}CH_2)_n\text{—}NHR^{10}$.

3. The process as recited in claim 2 wherein said 1,4-diphenylazetidinone derivatives are represented by the formula (IV):

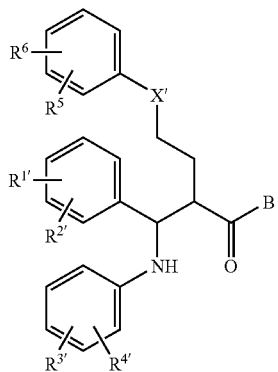

(IV)

wherein:
X' is X, or $CHOSi(alkyl)_o(aryl)_p$ with o, p=1 to 3 and o+p=3, $C(Oalkyl)_2$ or cyclic ketal such as $C[O(\text{—}CH_2)_qO]$ with q=2, 3

$R^{1'}$ and $R^{2'}$ are $R^1$, $R^2$, and —OH, wherein —OH is protected by a suitable protecting group; $R^3$ and $R^{4'}$ are $R^{30}$, $R^{40}$, $CH_2NHCO_2CH_2(C_6H_5)$, $CH_2N[Si(alkyl)_o(aryl)_p]$-$CO_2CH_2(C_6H_5)$, $CH_2NHCO_2$-tert.Bu, $CH_2N[Si(alkyl)_o(phenyl)_p]CO_2$-tert.Bu, $CH_2NHC(C_6H_5)_3$, $CH_2N\text{=}C(C_6H_5)_2$ or $CH_2N\text{=}CH[C_6H_4(R^6)]$ and;

-B=

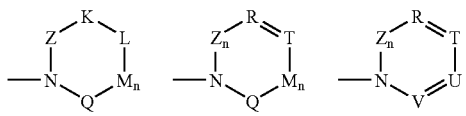

or -B=

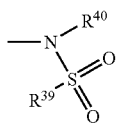

are reacted with said cyclization catalyst yielding intermediate compounds of formula (V),

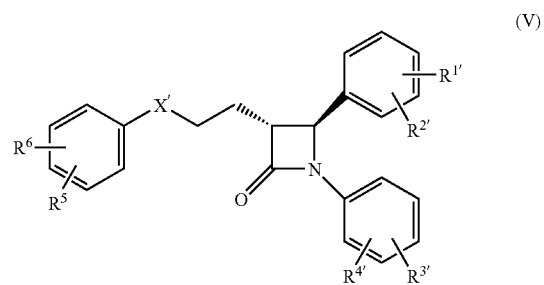

(V)

wherein $R^{1'}$-$R^4$, $R^5$ and $R^6$ are hereinbefore defined, which is then de-protected to yield the 1,4-diphenylazetidinone derivatives of formula (I).

4. The process as recited in claim 1 wherein compounds of formula (II)

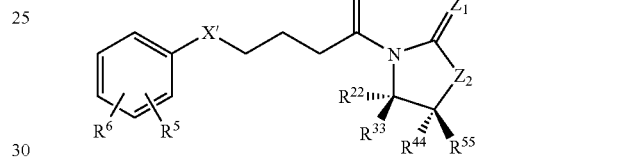

(II)

are reacted with imines of formula (III)

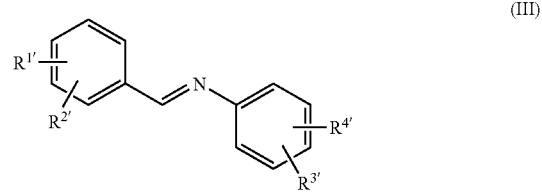

(III)

to give intermediates of formula (IV'),

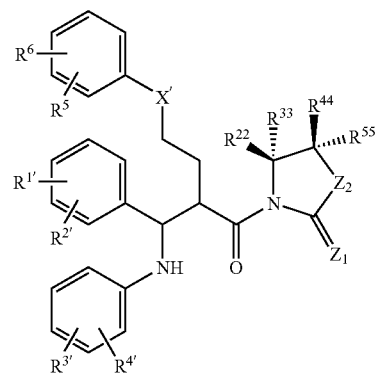

(IV')

which are then cyclized to precursor compounds of formula (V), which can be de-protected to give the compound (I),

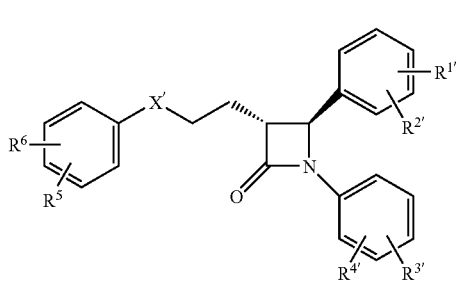

(V)

wherein the substituents are as defined above, including the following;
X' is selected from the group consisting of X, CHOSi(alkyl)$_o$(aryl)$_p$ with the stipulation that o and p=1 to 3 and o+p=3, and C(O-alkyl)$_2$ or a cyclic ketal selected from the group consisting of C[O(CH$_2$)$_q$O] with q=2, 3
$R^{22}$, $R^{33}$ and $R^{34}$, are independently selected from the group consisting of H, aryl or (C$_1$-C$_{10}$)alkyl
$Z_1$ and $Z_2$ are independently selected from the group consisting of O, NH, NR$^{15}$, or S
$R^{15}$ is aryl or (C$_1$-C$_{10}$)alkyl,
$R^1$ and $R^2$ are independently selected from the group consisting of $R^1$, $R^2$, $R^{10}$ and $R^{20}$.
$R^3$ and $R^4$ are independently selected from the group consisting of CH$_2$NHCO$_2$CH$_2$(C$_6$H$_5$), CH$_2$N[Si(alkyl)$_o$(aryl)$_p$]CO$_2$CH$_2$(C$_6$H$_5$), CH$_2$NHCO$_2$-tert.Bu, CH$_2$N[Si(alkyl)$_o$(phenyl)$_p$]CO$_2$-tert.Bu, CH$_2$NHC(C$_6$H$_5$)$_3$, CH$_2$N=C(C$_6$H$_5$)$_2$ or CH$_2$N=CH[C$_6$H$_4$(R$^6$)]
wherein the cyclization catalyst consists of a salt formed by the combination of a cation and an anion of the formula selected from the group consisting of:

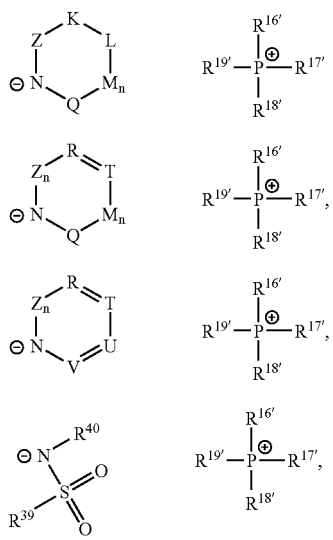

where, $R^{16'}$, $R^{17'}$, $R^{18'}$ and $R^{19'}$ are independently selected from the group consisting of aryl, (C$_1$-C$_{15}$)alkyl, and benzyl and the other substituents are as hereinbefore defined.

5. The process as recited in claim 4, wherein compounds of formula (II)

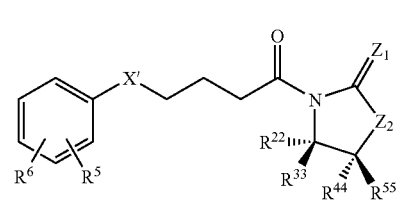

are reacted with imines of formula (III)

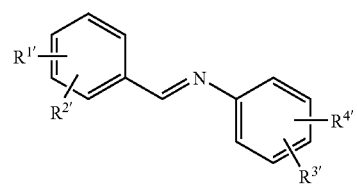

to give intermediates of formula (IV'),

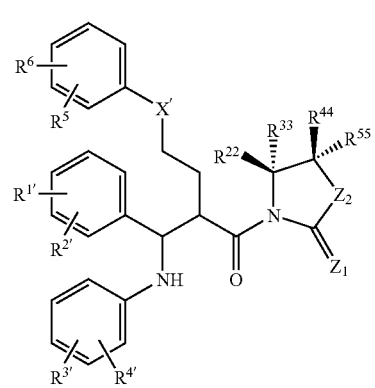

which are then cyclized to produce compounds of formula (V), which are then de-protected to give compound (I),

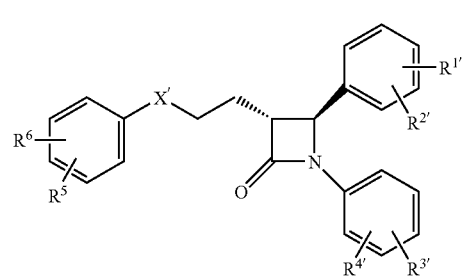

wherein
X' is selected from the group consisting of X, CHOSi(alkyl)$_o$(aryl)$_p$ with o, p=1 to 3 and o+p=3, C(Oalkyl)$_2$ or a cyclic ketal selected from the group consisting of C[O(—CH$_2$)$_q$—O] with q=2, 3
$R^{22}$, $R^{33}$, $R^{44}$ and $R^{55}$ are independently selected from the group consisting of H, aryl or (C$_1$-C$_{10}$)alkyl
$Z_1$ and $Z_2$ are independently selected from the group consisting of O, NH, NR$^5$, and S $R^{15}$ is aryl or $(C_1-C_{10})$alkyl, $R^{1'}$ and $R^{2'}$ is $R^1$, $R^2$, $R^{10}$ and $R^{20}$ and $R^{3'}$, $R^{4'}$ is selected from the group consisting of $R^3$, $R^4$, $CH_2NHCO_2CH_2(C_6H_5)$, $CH_2N[Si(alkyl)_o(aryl)_p]CO_2CH_2(C_6H_5)$, $CH_2NHCO_2$-tert.Bu, $CH_2N[Si(alkyl)_o(phenyl)_p]CO_2$-tert.Bu, $CH_2NHC(C_6H_5)_3$, $CH_2N=C(C_6H_5)_2$ or $CH_2N=CH[C_6H_4(R^6)]$ wherein the cation component of the cyclization catalyst corresponds to that of formula (XII), and the anion component is $R^{41}O^-$, or the cation component of the cyclization catalyst corresponds to that of the general formula (XII), and the anion is $R^{42}COO^-$, or the cation corresponds to formula (XII), and the anion is $Cl^-$, $Br^-$ or $I^-$, and these are combined with Ag2O, to form the cation, wherein $R^{16,\ R17}$, $R^{18}$, and $R^{19}$ are independently selected from the group consisting of aryl, $(C_1-C_{15})$alkyl, benzyl, $R^{41}$ is selected from the group consisting of aryl, $(C_1-C_{15})$ alkyl, benzyl, and $R_{42}$ is selected from the group consisting of $(C_1-C_{15})$alkyl, benzyl, $(C_5-C_8)$cycloalkyl, aryl, where aryl may be substituted by F, Cl, Br, I, —OH, —O$(C_1-C_3)$alkyl, —NH$_2$, —NH$(C_1-C_3)$alkyl, —N$[(C_1-C_3)$alkyl$]_2$, —C(O)OH, —C(O)O$(C_1-C_3)$alkyl, —C(O)NH$_2$, —C(O)NH$(C_1$-$C_3)$alkyl, —C(O)N$[(C_1-C_3)$alkyl$]_2$, —SO$_2$NH$_2$, —SO$_2$NH$(C_1-C_3)$alkyl, —SO2N$[(C_1-C_3)$alkyl$]_2$, CN, $(C_1-C_{12})$alkyl and $(C_5-C_8)$cycloalkyl.

6. The process as recited in claim 4 wherein compounds of formula (II)

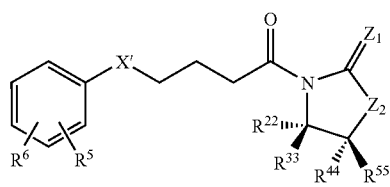

(II)

are reacted with imines of formula (III)

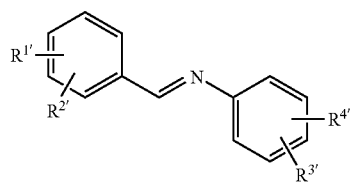

(III)

to produce intermediates of formula (IV'),

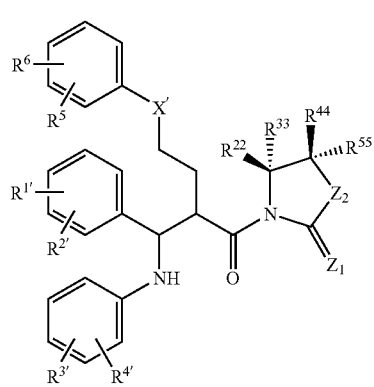

(IV')

which are then reacted with said cyclization catalyst to produce intermediate compounds of formula (V),

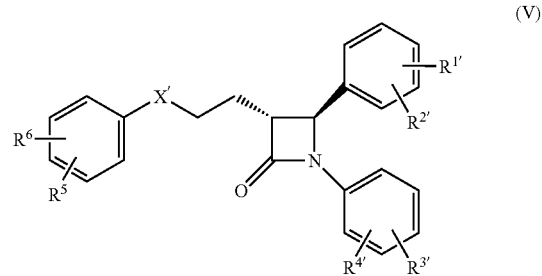

(V)

wherein the substituents of said formula II, III, IV' and V are as hereinbefore defined, and;

X' is selected from the group consisting of X, CHOSi(alkyl)$_o$(aryl)$_p$ with o and p=1 to 3 and o+p=3, C(Oalkyl)$_2$ or cyclic ketal such as C[O(—CH$_2$)$_q$—O] with q=2, 3 and $R^{22}$, $R^{33}$, $R^{44}$ and $R^{55}$ are independently selected from the group consisting of H, aryl or $(C_1-C_{10})$ alkyl; and, $Z^1$ and $Z^2$ are selected from the group consisting of O, NH, NR$^{15}$, or S;

$R^{15}$ is selected from the group consisting of aryl or $(C_1-C_{10})$ alkyl, $R^{1'}$ and $R^{2'}$ are $R^1$ and $R^2$ and —OH, wherein —OH is protected by a suitable protecting group;

$R^{3'}$, $R^{4'}$ are selected from the group consisting of $R^3$, $R^4$, $CH_2NHCO_2CH_2(C_6H_5)$, $CH_2N[Si(alkyl)_o(aryl)_p]$-$CO_2CH_2(C_6H_5)$, $CH_2NHCO_2$-tert.Bu, $CH_2N[Si(alkyl)_o$ (phenyl)$_p$]CO$_2$-tert.Bu, $CH_2NHC(C_6H_5)_3$, $CH_2N=C(C_6H_5)_2$ or $CH_2N=CH[C_6H_4(R^6)]$ wherein the cation in the cyclization catalyst corresponds to that of the formula (XII), and the anion is $R^{42}COO^-$, wherein $R^{16}$, $R^{17}$, $R^{18}$, and $R^{19}$ are independently are selected from the group consisting of aryl, $(C_1-C_{10})$alkyl, benzyl;

$R^{41}$ is aryl, $(C_1-C_{10})$alkyl, benzyl, and, $R^{42}$ is selected from the group consisting of $(C_1-C_{15})$alkyl, benzyl, $(C_5-C_5)$cycloalkyl, aryl, where aryl may be substituted by F, Cl, Br, I, —OH, —O$(C_1-C_3)$alkyl, —NH$_2$, —NH$(C_1-C_3)$alkyl, —N$[(C_1-C_3)$alkyl$]_2$, —C(O)OH, —C(O)O$(C_1-C_3)$alkyl, —C(O)NH$_2$, —C(O)NH$(C_1$-$C_3)$alkyl, —C(O)N$[(C_1-C_3)$alkyl$]_2$, —SO$_2$NH$_2$, —SO$_2$NH$(C_1-C_3)$alkyl, —SO$_2$N$[(C_1-C_3)$alkyl$]_2$, CN, $(C_1-C_{12})$alkyl and $(C_5-C_6)$cycloalkyl, which are then de-protected to yield compound (I).

7. The process as recited in claim 6, wherein the cation of the cyclization catalyst is a phosphonium cation of formula (XII) in which the radicals $R^{16'}$ to $R^{19'}$ are $(C_1$ to $C_{10})$alkyl.

8. The process as recited in claim 7, wherein the cation of the cyclization catalyst of formula (XII) is tetra-(n)-butylphosphonium.

9. The process as recited claim 8 wherein the anion of the cyclization catalyst is the anion of a cyclic imide of formula (VIII) or (IX).

10. The process as recited in claim 9 wherein the anion of the cyclization catalyst is the anion of an oxazolidinone of formula (VIII).

11. The process as recited in claim 10 wherein said radicals $R^{16'}$ to $R^{19'}$ are identical alkyl radicals.

12. The process as recited in claim 3 wherein when B is selected from the group consisting of the formula

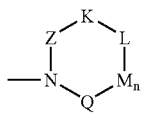

the catalyst is formulae (VIa):

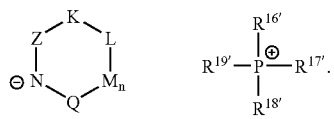
(VIa)

13. The process as recited in claim 3 wherein when B is selected from the group consisting of the formula

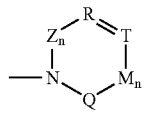

the catalyst is formulae (VIb),

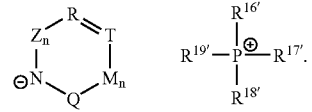
(VIb)

14. The process as recited in claim 3 wherein when B is selected from the group consisting of formula:

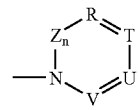

the catalyst is:

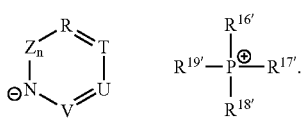
(VIc)

15. The process as recited in claim 3 wherein when B is selected from the group consisting of formula

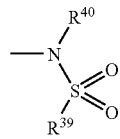

the catalyst is

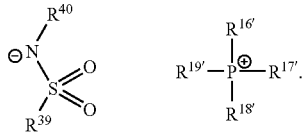
(VII)

* * * * *